(12) United States Patent
Keenan et al.

(10) Patent No.: US 7,829,713 B2
(45) Date of Patent: Nov. 9, 2010

(54) THERAPEUTIC PIPERAZINES

(75) Inventors: Terrence P. Keenan, Bay Shore, NY (US); Alan P. Kaplan, Kings Park, CA (US)

(73) Assignee: Helicon Therapeutics, Inc., San Diego, CA (US)

( * ) Notice: Subject to any disclaimer, the term of this patent is extended or adjusted under 35 U.S.C. 154(b) by 685 days.

(21) Appl. No.: 11/679,782

(22) Filed: Feb. 27, 2007

(65) Prior Publication Data

US 2007/0203124 A1 Aug. 30, 2007

Related U.S. Application Data

(60) Provisional application No. 60/777,291, filed on Feb. 28, 2006.

(51) Int. Cl.
- *C07D 241/04* (2006.01)
- *C07D 241/08* (2006.01)
- *C07D 403/04* (2006.01)
- *C07D 403/06* (2006.01)
- *C07D 243/08* (2006.01)
- *C07D 265/30* (2006.01)
- *C07D 401/06* (2006.01)
- *C07D 405/04* (2006.01)

(52) U.S. Cl. .................. 544/383; 544/373; 544/389; 544/391; 544/392; 544/394; 544/395; 544/174; 544/230; 544/360; 544/370; 544/371; 544/390; 540/450; 540/485; 540/491; 540/575

(58) Field of Classification Search ............... 544/392, 544/394, 395

See application file for complete search history.

(56) References Cited

U.S. PATENT DOCUMENTS

| | | | |
|---|---|---|---|
| 2,996,507 A * | 8/1961 | Sommers .................. 544/395 |
| 3,306,903 A | 2/1967 | Padam et al. | |
| 3,857,945 A * | 12/1974 | Najer et al. ............ 514/255.03 |
| 4,093,726 A | 6/1978 | Winn et al. | |
| 5,086,055 A * | 2/1992 | Walsh et al. ........... 514/254.02 |
| 6,555,572 B2 | 4/2003 | Lauener et al. | |
| 6,953,801 B2 * | 10/2005 | Hutchison et al. .......... 514/249 |
| 7,429,666 B2 | 9/2008 | Lachance et al. | |
| 7,439,243 B2 | 10/2008 | Johnson et al. | |
| 7,589,199 B2 | 9/2009 | Pennell et al. | |
| 7,625,889 B2 | 12/2009 | Eastwood et al. | |

2003/0220352 A1 11/2003 Lauener et al.

FOREIGN PATENT DOCUMENTS

| | | |
|---|---|---|
| DE | 23 45 422 | 3/1975 |
| EP | 0 185 909 | 7/1986 |
| EP | 0 202 760 | 11/1986 |
| EP | 0 277 725 | 8/1988 |
| EP | 0 511 879 | 11/1992 |
| EP | 0 527 081 | 2/1993 |
| FR | 2 551 753 | 3/1985 |
| GB | 1 575 904 | 10/1980 |
| GB | 2 101 580 | 1/1983 |
| WO | 200168600 A2 | 9/2001 |
| WO | WO 2004/024728 | 3/2004 |
| WO | WO 2004/103998 | 12/2004 |
| WO | WO 2006/111549 | 10/2006 |

OTHER PUBLICATIONS

Ferrand, G. et al., Synthesis of new 1,2,3-traizin-4-ones as Potential anti-Depressants. Synthese et Activite Anti-Depressive Potentielle De Nouvelles Traizine-1,2,3 Ones-4 European Journal of Medicinal Chemistry, Editions Scientifique Elsevier, Paris, FR, vol. 22, No. 4 (1987) pp. 337-345 XP002396679 ISSN: 0223-5234.

Bosc, J. J. et al.: "Synthesis and Antidepressant Activity of 5-(1-aryl-4-piperazino) Methyl-2-Amino-2-Oxazolines" European Journal of Medicinal Chemistry, 27(5), pp. 437-442 Coden: EJMCA5; ISSN: 0223-5234 (1992) XP002444447.

Heinrich, T et al., :Indolebutylamines as Selective 5-HT1A Agonists Journal of medicinal Chemistry, 47(19), pp. 4677-4683 Coden: JMCMAR; ISSN: 0022-2623 (2004) XP002444448.

* cited by examiner

*Primary Examiner*—Emily Bernhardt
(74) *Attorney, Agent, or Firm*—Sheppard, Mullin, Richter & Hampton LLP; Don J. Pelto

(57) ABSTRACT

The invention includes a compound of formula I:

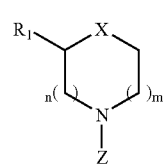

(I)

wherein $R_1$, X, Z, n, and m have any of the values described herein, as well as salts of such compounds, compositions comprising such compounds, and therapeutic methods that comprise the administration of such compounds. The compounds are inhibitors of PDE4 function and are useful for improving cognitive function in animals.

3 Claims, 2 Drawing Sheets

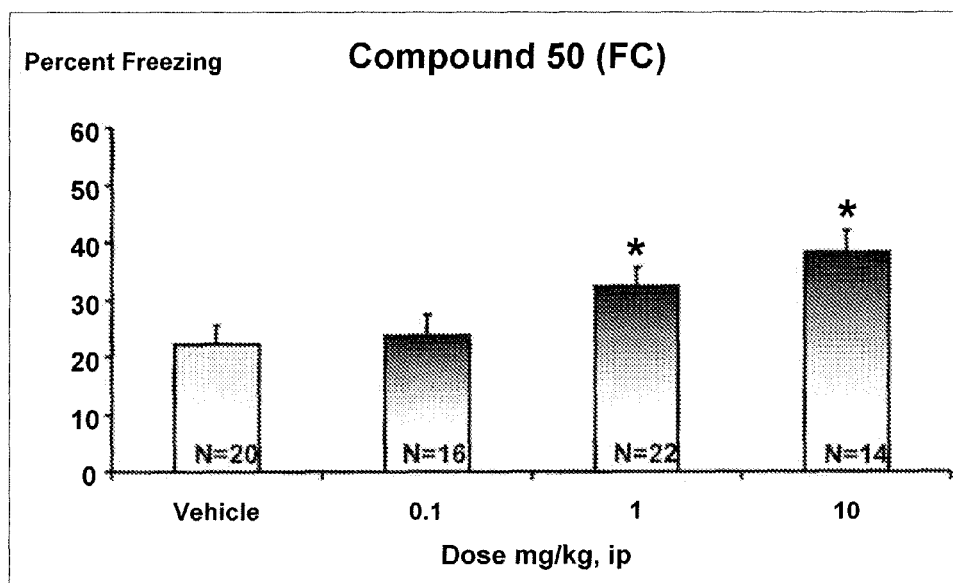
Figure 1. Effects of Compound 50 on contextual memory (fear conditioning, FC) in mice. 1 and 10 mg/kg Compound 50 injected 20 minutes before training significantly enhanced contextual memory in mice.

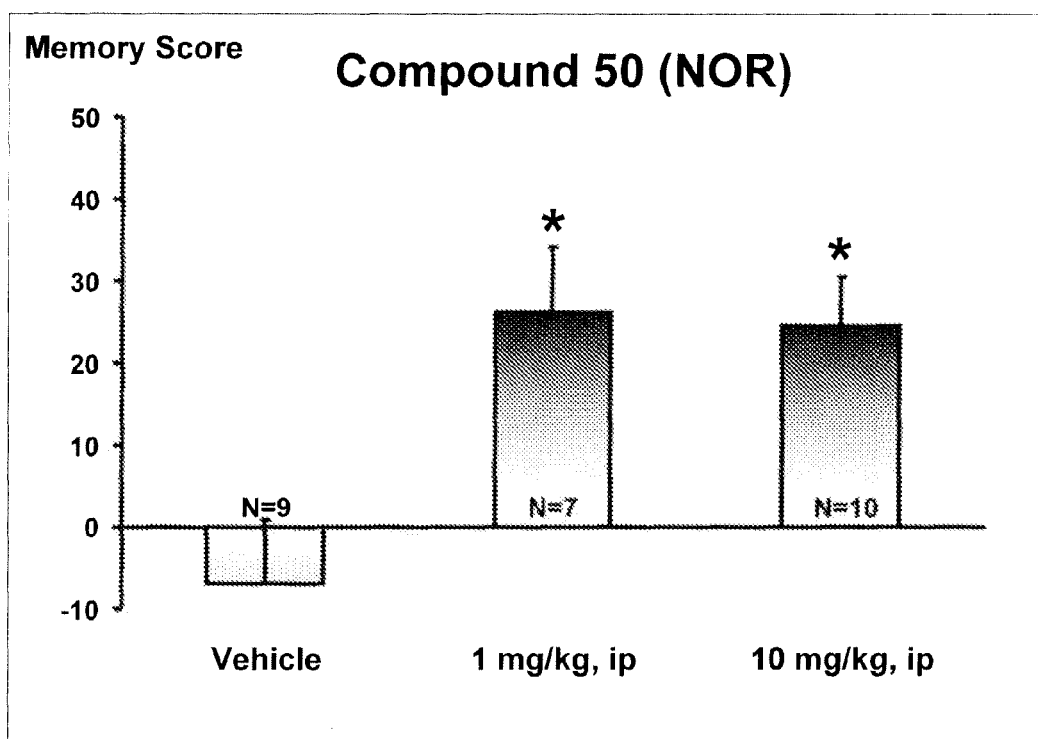
Figure 2. Effects of Compound 50 on novel object recognition (NOR) in C57Bl/6 mice. 24 hour memory in object recognition is deficient in C57BL/6 mice. Injections of 1 and 10 mg/kg Compound 50 20 min before training ameliorate long-term memory deficit in C57Bl/6 mice.

THERAPEUTIC PIPERAZINES

CROSS-REFERENCE TO RELATED APPLICATIONS

This is a non-provisional application 37 C.F.R. §153(b), claiming priority under 37 C.F.R. §119(e) to U.S. Provisional Patent Application Ser. No. 60/777,291, filed on Feb. 28, 2006, the entire disclosure of which is hereby expressly incorporated by reference.

BACKGROUND OF INVENTION

An estimated 4 to 5 million Americans (about 2% of all ages and 15% of those older than 65) have some form and degree of cognitive failure. Cognitive failure (dysfunction or loss of cognitive functions, the process by which knowledge is acquired, retained and used) commonly occurs in association with central nervous system (CNS) disorders or conditions, including age-associated memory impairment, delirium (sometimes called acute confusional state), dementia (sometimes classified as Alzheimer's or non-Alzheimer's type), Alzheimer's disease, Parkinson's disease, Huntington's disease (chorea), mental retardation (e.g. Rubenstein-Taybi Syndrome), cerebrovaslular disease (e.g. stroke, ischemia), affective disorders (e.g. depression), psychotic disorders (e.g., schizophrenia, autism (Kanner's Syndrome)), neurotic disorders (i.e. anxiety, obsessive-compulsive disorder), attention deficit disorder (ADD), subdural hematoma, normal-pressure hydrocephalus, brain tumor, head or brain trauma.

Cognitive dysfunction is typically manifested by one or more cognitive deficits, which include memory impairment (inability to learn new information or to recall previously learned information), aphasia (language/speech disturbance), apraxia (impaired ability to carry out motor activities despite intact motor function), agnosia (failure to recognize or identify objects despite intact sensory function), disturbance in executive functioning (i.e. planning, organizing, sequencing, abstracting).

Cognitive dysfunction causes significant impairment of social and/or occupational functioning, which can interfere with the ability of an individual to perform activities of daily living and greatly impact the autonomy and quality of life of the individual. Thus, there is currently a need for compounds and methods that are useful for improving cognitive function in animals.

Phosphodiesterases (E.C. 3.1.4.17) are a class of enzymes that catalyze the hydrolysis of the 3'-phosphodiester bond of 3',5'-cyclic nucleotides. The phosphodiesterase 4 (PDE4) isoform specifically hydrolyzes adenonsine 3',5' cyclic monophosphate (cAMP) to form 5'-adenosine monophosphate (5'-AMP). cAMP is a well studied intracellular second messenger that is known to be responsible for regulating a number of cellular processes including transcriptional regulation. One signaling pathway known to be regulated by intracellular levels of cAMP is the CREB pathway. The CREB pathway is responsible for regulating transcriptional activity in the brain (including the hippocampus) that leads to protein syntheses required for learning and memory, especially the consolidation of short-term to long-term memory. It is known that inhibition of PDE4 improves cognitive function in mammals, including contextual memory and object recognition (Tully, et. al., *Nature Reviews Drug Discovery*, 2003, 2, 267-277; and Barad, et al., *Proc. Natl. Acad. Sci.* 1998, 95, 15020-15025). It has also been shown to improve memory in animals with impaired CREB function (see Bourtchouladze, et. al., *Proc Natl Acad Sci USA,* 2003, 100, 10518-10522).

Numerous companies have invested in the development of specific PDE4 inhibitors to treat a variety of diseases, most notably in the anti-inflammatory field (e.g. Rolipram™, and Ariflo™). A common side-effect of these treatments has been the induction of emesis. Accordingly, there is a particular need for PDE4 inhibiting compounds that cause little or no emesis.

SUMMARY OF THE INVENTION

The invention relates to compounds that inhibit PDE4 and that are useful to improve cognitive function. Accordingly, in one embodiment the invention provides a compound of formula I:

wherein:

$R_1$ is H, $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, $(C_3-C_8)$cycloalkyl, $(C_3-C_8)$cycloalkyl$(C_1-C_6)$alkyl, halo$(C_1-C_6)$alkyl, aryl, aryl$(C_1-C_6)$alkyl, aryl$(C_1-C_6)$alkoxy, aryl$(C_1-C_6)$alkanoyl, het, het$(C_1-C_6)$alkyl, het$(C_1-C_6)$alkoxy, or het$(C_1-C_6)$alkanoyl;

n is 1 or 2;

m is 1 or 2;

W is O, S, or two hydrogens;

X is O or N—Y—$R_4$;

Y is a direct bond, —$CH_2$—, —C(=O)—, —C(=S)—, —O—, —C(=O)O—, —OC(=O)—, —C(=O)$NR_a$—, —S—, —S(=O)—, —S(=O)$_2$—, or —S(=O)$_2$$NR_a$—;

$R_4$ is H, $(C_1-C_6)$alkyl, $(C_1-C_6)$alkoxy, $(C_1-C_6)$alkanoyl, hydroxy, $(C_3-C_8)$cycloalkyl, $(C_3-C_8)$cycloalkyl$(C_1-C_6)$alkyl, halo$(C_1-C_6)$alkyl, hydroxy$(C_1-C_6)$alkyl, $(C_1-C_6)$alkoxycarbonyl, carboxy, aryl, aryl$(C_1-C_6)$alkyl, het, $NR_dR_e$, —C(=O)$NR_dR_e$, $NR_dR_e(C_1-C_6)$alkyl, or het$(C_1-C_6)$alkyl;

$R_a$ is H, $(C_1-C_6)$alkyl, $(C_3-C_8)$cycloalkyl, $(C_1-C_6)$alkoxy$(C_2-C_6)$alkyl, or $(C_3-C_8)$cycloalkyl$(C_1-C_6)$alkyl;

Z is a phenyl ring substituted with one or more substituents independently selected from $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_1-C_6)$alkoxy, $(C_3-C_8)$cycloalkyloxy, and $(C_3-C_8)$cycloalkyl$(C_1-C_6)$alkoxy; or Z is a phenyl ring that is fused to a saturated, partially unsaturated, or aromatic, mono- or bicyclic ring system comprising from about 3 to about 8 atoms selected from carbon, oxygen, and $NR_b$, wherein the mono- or bicyclic ring system of Z is optionally substituted with one or more $R_c$, and wherein the phenyl ring that is fused to the mono- or bicyclic ring system is optionally substituted with one or more substituents independently selected from $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_2-C_6)$alkoxy, $(C_3-C_8)$cycloalkyloxy, and $(C_3-C_8)$cycloalkyl$(C_1-C_6)$alkoxy;

$R_b$ is absent, H, $(C_1-C_6)$alkyl, $(C_3-C_8)$cycloalkyl, $(C_1-C_6)$alkoxy$(C_2-C_6)$alkyl, or $(C_3-C_8)$cycloalkyl$(C_1-C_6)$alkyl;

$R_c$ is $(C_1-C_6)$alkyl, $(C_1-C_6)$alkoxy, $(C_1-C_6)$alkanoyl, $(C_1-C_6)$alkoxycarbonyl, $(C_1-C_6)$alkanoyloxy, $(C_3-C_8)$cycloalkyl, $(C_3-C_8)$cycloalkyl$(C_1-C_6)$alkyl, halo$(C_1-C_6)$alkyl, aryl, aryl$(C_1-C_6)$alkyl, aryl$(C_1-C_6)$alkoxy, aryl$(C_1-C_6)$alkanoyl, het, het$(C_1-C_6)$alkyl, het$(C_1-C_6)$alkoxy, or het$(C_1-C_6)$alkanoyl;

each $R_d$ and $R_e$ is independently H, hydroxy, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, $(C_1-C_6)$alkanoyl, $(C_1-C_6)$alkoxycarbonyl, $(C_3-C_8)$cycloalkyl, $(C_3-C_8)$cycloalkyl$(C_1-C_6)$alkyl, aryl, aryl$(C_1-C_6)$alkyl, $NR_fR_g$, or aryl$(C_1-C_6)$alkoxy; and each $R_f$ and $R_g$ is independently H, $(C_1-C_6)$alkyl, $(C_1-C_6)$alkoxy, $(C_1-C_6)$alkanoyl, $(C_1-C_6)$alkoxycarbonyl, $(C_3-C_8)$cycloalkyl, $(C_3-C_8)$cycloalkyl$(C_1-C_6)$alkyl, aryl, aryl$(C_1-C_6)$alkyl, or aryl$(C_1-C_6)$alkoxy; or $R_f$ and $R_g$ together with the nitrogen to which they are attached form a pyrrolidino, piperidino, piperazino, morpholino, or thiomorpholino ring;

wherein any aryl or het of $R_1$ or $R_4$ is optionally substituted with one or more substitutents independently selected from $(C_1-C_6)$alkyl, phenyl, $(C_1-C_6)$alkoxy, $(C_1-C_6)$alkanoyl, $(C_1-C_6)$alkoxycarbonyl, $(C_1-C_6)$alkanoyloxy, $(C_3-C_8)$cycloalkyl, $(C_3-C_8)$cycloalkyl$(C_1-C_6)$alkyl, halo$(C_1-C_6)$alkyl, $(C_3-C_8)$cycloalkyloxy, $(C_3-C_8)$cycloalkyl$(C_1-C_6)$alkoxy, halo$(C_2-C_6)$alkoxy, cyano, nitro, halo, carboxy or $NR_dR_e$;

and wherein the ring containing X is optionally substituted on carbon with one or more halo, $(C_1-C_6)$alkyl, or $(C_1-C_6)$alkoxy.

or a pharmaceutically acceptable salt thereof.

The invention also provides a pharmaceutical composition comprising a compound of formula I, or a pharmaceutically acceptable salt thereof, in combination with a pharmaceutically acceptable diluent or carrier.

The invention also provides a therapeutic method for improving cognitive function in an animal comprising administering to the animal an effective amount of a compound of formula I, or a pharmaceutically acceptable salt thereof.

The invention also provides a method for inhibiting PDE4 receptors (in vitro or in vivo) comprising contacting the receptors with an effective inhibitory amount of a compound of formula I, or a pharmaceutically acceptable salt thereof.

The invention also provides a therapeutic method for treating a disease or condition in an animal wherein the activity of PDE4 receptors is implicated and inhibition of PDE4 receptor activity is desired comprising administering to the animal an effective PDE4 inhibiting amount of a compound of formula I, or a pharmaceutically acceptable salt thereof.

The invention also provides a method for activating the CREB pathway in an animal comprising administering to the animal an effective CREB pathway activating amount of a compound of formula I, or a pharmaceutically acceptable salt thereof.

The invention also provides a method for activating the CREB pathway in vitro comprising contacting a sample comprising SK-N-MC cells stably expressing a CRE-luciferase construct with an effective CREB pathway activating amount of a compound of formula I, or a pharmaceutically acceptable salt thereof.

The invention also provides a therapeutic method for treating a psychiatric disorder in an animal comprising administering to an animal in need thereof an effective amount of a compound of formula I, or a pharmaceutically acceptable salt thereof.

The invention provides a compound of formula I, or a pharmaceutically acceptable salt thereof for use in medical therapy (e.g. for use in improving cognitive function or for use in treating a disease or condition wherein inhibition of PDE4 receptor function is indicated or for treating a psychiatric disorder), as well as the use of a compound of formula I for the manufacture of a medicament useful for improving cognitive function in an animal.

The invention also provides the use of a compound of formula I, or a pharmaceutically acceptable salt thereof for the manufacture of a medicament useful for inhibiting PDE4 receptors in an animal.

The invention also provides the use of a compound of formula I, or a pharmaceutically acceptable salt thereof for the manufacture of a medicament useful for activating the CREB pathway in an animal.

The invention also provides the use of a compound of formula I, or a pharmaceutically acceptable salt thereof for the manufacture of a medicament useful for treating a psychiatric disorder in an animal.

The invention also provides synthetic processes and intermediated disclosed herein that are useful for preparing compounds of formula (I) or salts thereof. Some compounds of formula I may be useful as intermediates for preparing other compounds of formula I.

Representative compounds of formula I have also been tested and found to produce little or no emesis.

BRIEF DESCRIPTION OF THE FIGURES

FIG. 1 shows data for a representative compound of the invention 50 in the Contextual Memory Assay (fear conditioning) described hereinbelow.

FIG. 2 shows data for a representative compound of the invention 50 in the novel object recognition (NOR) assay described hereinbelow.

DETAILED DESCRIPTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic; Het encompasses a radical of a monocyclic, bicyclic, or tricyclic ring system containing a total of 3-20 atoms, including one or more (e.g., 1, 2, 3, 4, 5, or 6) carbon atoms, and one or more (e.g., 1, 2, 3, or 4) heteroatoms selected from oxygen, sulfur, and N(X) wherein X is absent or is H, O, $(C_1-C_4)$alkyl, phenyl or benzyl, wherein one or more ring carbons of Het can optionally be substituted with oxo (=O); Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. The term Het encompasses Heteroaryl. Aryl$(C_1-C_6)$alkyl is an alkyl group substituted with one or more aryl groups; Het$(C_1-C_6)$alkyl is an alkyl group substituted with one or more Het groups; and Heteroaryl($C_1$-$C_6$)alkyl is an alkyl group substituted with one or more Heteroaryl groups.

The term "animal" as used herein includes birds, reptiles, and mammals (e.g. domesticated mammals and humans).

The term "psychiatric disorder" as used herein includes psychotic disorders, neurological disorders and neurotic disorders. The term includes schizophrenia, age-associated memory impairment (AAMI); mild cognitive impairment (MCI), delirium (acute confusional state); depression, dementia (sometimes further classified as Alzheimer's or non-Alzheimer's type dementia); Alzheimer's disease; Parkinson's disease; Huntington's disease (chorea); mental retardation; (e.g., Rubenstein-Taybi and Downs Syndrome); cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) or brain trauma It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine PDE4 inhibiting activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_8$)cycloalkyl can be cyclopropyl, cyclobutyl, cyclopentyl, or cyclohexyl; ($C_3$-$C_8$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$) alkoxy can be methoxy, ethoxy, propoxy, isopropoxy, butoxy, iso-butoxy, sec-butoxy, pentoxy, 3-pentoxy, or hexyloxy; ($C_1$-$C_6$)alkanoyl can be acetyl, propanoyl or butanoyl; halo ($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; ($C_1$-$C_6$) alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$-$C_6$)alkanoyloxy can be acetoxy, propanoyloxy, butanoyloxy, isobutanoyloxy, pentanoyloxy, or hexanoyloxy; ($C_3$-$C_8$)cycloalkyloxy can be cyclopropyloxy, cyclobutyloxy, cyclopropyloxy, cyclohexyloxy, or cyclohexyloxy; aryl can be phenyl, indenyl, or naphthyl; and heteroaryl can be furyl, imidazolyl, triazolyl, triazinyl, oxazolyl, isoxazolyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is ($C_1$-$C_6$)alkoxy, ($C_1$-$C_6$)alkanoyl, ($C_1$-$C_6$)alkoxycarbonyl, ($C_1$-$C_6$)alkanoyloxy, ($C_3$-$C_8$)cycloalkyl, ($C_3$-$C_8$)cycloalkyl($C_1$-$C_6$)alkyl, halo($C_1$-$C_6$)alkyl, aryl, aryl($C_1$-$C_6$)alkyl, aryl($C_1$-$C_6$)alkoxy, aryl($C_1$-$C_6$)alkanoyl, het, het($C_1$-$C_6$)alkyl, het($C_1$-$C_6$)alkoxy, or het($C_1$-$C_6$)alkanoyl.

A specific value for $R_1$ is H, ($C_1$-$C_6$)alkyl, aryl, aryl($C_1$-$C_6$)alkyl, or het.

A specific value for $R_1$ is H, benzyl, indolyl, phenyl, 2-methylpropyl, 2-methylbenzyl, 3-methylbenzyl, 4-methylbenzyl, α-phenylbenzyl, phenethyl, 1-naphthylmethyl, 2-naphthylmethyl, 4-phenylbenzyl, 4-ethoxybenzyl, isopropyl, cyclohexylmethyl, 2-methoxyphenyl, 3-methoxyphenyl, or 4-methoxyphenyl.

A specific value for n is 1.
A specific value for n is 2.
A specific value for m is 1.
A specific value for m is 2.
A specific value for X is N—Y—$R_4$.
A specific value for Y is a direct bond, —$CH_2$—, —C(=O)—, or —S(=O)$_2$—.

A specific value for $R_4$ is H, ($C_1$-$C_6$)alkyl, ($C_1$-$C_6$)alkoxy, ($C_1$-$C_6$)alkanoyl, hydroxy($C_2$-$C_6$)alkyl, ($C_1$-$C_6$)alkoxycarbonyl, carboxy, aryl, aryl($C_1$-$C_6$)alkyl, het, $NR_d$—C(=O)$NR_dR_e$, or het($C_1$-$C_6$)alkyl.

A specific value for Y—$R_4$ is H, tert-butoxycarbonyl, formylmethyl, pyridylmethyl, methyl, ethylaminocarbonyl, ethylsulfonyl, benzylsulfonyl, benzyl, acetyl, methoxycarbonylmethyl, methylsulfonyl, ethyl, carboxymethyl, propyl, 2-hydroxyethyl, methoxyaminocarbonylmethyl, benzyloxyaminocarbonylmethyl, prop-2-eneyloxyaminocarbonylmethyl, hydroxyaminocarbonylmethyl, hydroxyacetyl, 2-methylhydrazocarbonylmethyl, hydrazocarbonylmethyl, 2,2-dimethylhydrazo-carbonylmethyl, or ethoxycarbonyl.

A specific value for Z is a phenyl ring substituted with one or more substituents independently selected from ($C_1$-$C_6$) alkoxy, halo($C_1$-$C_6$)alkoxy, ($C_3$-$C_8$)cycloalkoxy, and ($C_3$-$C_8$) cycloalkyl($C_1$-$C_6$)alkoxy.

A specific value for Z is a phenyl ring that is fused to a saturated, partially unsaturated, or aromatic, mono- or bicyclic ring system comprising from about 3 to about 8 atoms selected from carbon, oxygen, and $NR_b$, wherein the mono- or bicyclic ring system of Z is optionally substituted with one or more $R_c$, and wherein the phenyl ring that is fused is fused to the mono- or bicyclic ring system is optionally substituted with one or more substituents independently selected from ($C_1$-$C_6$)alkyl, halo($C_1$-$C_6$)alkyl, ($C_3$-$C_8$)cycloalkyl, ($C_3$-$C_8$) cycloalkyl($C_1$-$C_6$)alkyl, ($C_1$-$C_6$)alkoxy, halo($C_2$-$C_6$)alkoxy, ($C_3$-$C_8$)cycloalkyloxy, and ($C_3$-$C_8$)cycloalkyl($C_1$-$C_6$)alkoxy.

A specific group of compounds of formula I are compounds wherein Z has the following formula:

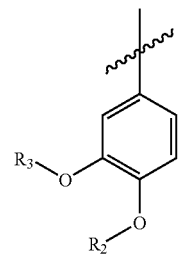

wherein
$R_2$ is ($C_1$-$C_6$)alkyl, or halo($C_1$-$C_6$)alkyl; and
$R_3$ is ($C_1$-$C_6$)alkyl, halo($C_1$-$C_6$)alkyl, ($C_3$-$C_8$)cycloalkyl, or ($C_3$-$C_8$)cycloalkyl($C_1$-$C_6$)alkyl.

A specific value for $R_2$ is methyl and $R_3$ is cyclopropyl.

A specific group of compounds of formula I are compounds wherein Z is selected from a structure of formula III, IV, and V:

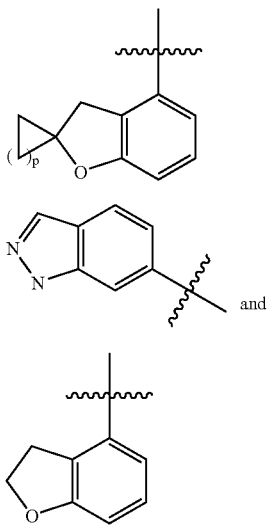

that is optionally substituted with one or more substituents selected from $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_2-C_6)$alkoxy, $(C_3-C_8)$cycloalkyloxy, and $(C_3-C_8)$cycloalkyl$(C_1-C_6)$alkoxy; wherein p is 1, 2, 3, 4, 5, or 6.

A specific group of compounds of formula I are compounds wherein Z is selected from a structure of formula VI, VII, and VIII:

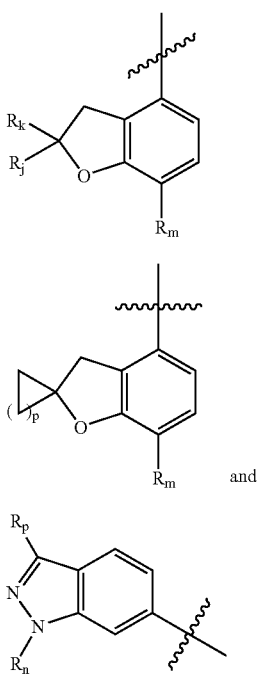

wherein:
$R_j$, $R_k$, $R_m$, $R_n$, and $R_p$ are each independently selected from H, $(C_1-C_6)$alkyl, halo$(C_1-C_6)$alkyl, $(C_3-C_8)$cycloalkyl, $(C_3-C_8)$cycloalkyl$(C_1-C_6)$alkyl, $(C_1-C_6)$alkoxy, halo$(C_2-C_6)$alkoxy, $(C_3-C_8)$cycloalkyloxy, and $(C_3-C_8)$cycloalkyl$(C_1-C_6)$alkoxy; and p is 1, 2, 3, 4, 5, or 6.

A specific group of compounds of formula I are compounds wherein $R_j$ and $R_k$ are independently selected from H and methyl; $R_m$ is methoxy; $R_n$ is cyclopentyl; $R_p$ is ethyl; and p is 3.

A specific group of compounds of formula I are compounds of formula IX:

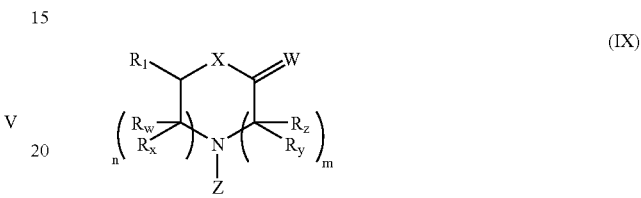

(IX)

wherein $R_1$, X, W, Z, n and m have any of the values or specific values defined herein and wherein $R_w$, $R_x$, $R_y$, and $R_z$, are each independently H, halo, or $(C_1-C_6)$alkyl.

A specific group of compounds of formula I are compounds of formula X:

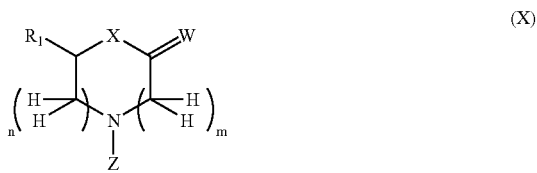

(X)

wherein $R_1$, X, W, Z, n and m have any of the values or specific values defined herein.

Specific compounds of formula I are presented in the Examples below (e.g. compounds 49-120).

Processes for preparing compounds of formula I are provided as further embodiments of the invention and are illustrated by the following procedures in which the meanings of the generic radicals are as given above unless otherwise qualified.

In one embodiment the invention provides a method for preparing a compound of formula I or a salt thereof as described herein comprising:
a) deprotecting a corresponding compound that comprises one or more protecting groups to provide the compound of formula I;
b) forming a pharmaceutically acceptable salt from a compound of formula I; or
c) converting a compound of formula I wherein X is N—Y—$R_4$ and Y—$R_4$ taken together is H to a corresponding compound of formula I wherein Y—$R_4$ is other than H.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 100 mg/kg, e.g., from about 10 to about 75 mg/kg of body weight per day, such as 3 to about 50 mg per kilogram body weight of the recipient per day, preferably in the range of 0.5 to 90 mg/kg/day, most preferably in the range of 1 to 60 mg/kg/day The compound is conveniently administered in unit dosage form; for example, containing 1 to 1000 mg, conveniently 10 to 750 mg, most conveniently, 50 to 500 mg of active ingredient per unit dosage form. Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s). The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds of the invention can also optionally be administered in combination with one or more other therapeutic agents that are effective to improve cognition or treat a psychiatric disorder and/or one or more therapeutic agents that are effective to treat age-associated memory impairment (AAMI); mild cognitive impairment (MCI) delirium (acute confusional state); dementia (sometimes further classified as Alzheimer's or non-Alzheimer's type dementia); Alzheimer's disease; Parkinson's disease; Pick's Disease, multiple sclerosis, Huntington's disease (chorea); mental retardation; (e.g., Rubenstein-Taybi, Fragile X, Angelman Syndrome, Coffin-Lowry Syndrome and Downs Syndrome); Wilson's Disease, Creutzfeldt-Jacob Disease, Neurofibromatosis type 1, Wernicke-Korsakoff Syndrome, cerebrovascular disease (e.g., vascular dementia, post-cardiac surgery); affective disorders; psychotic disorders; autism (Kanner's Syndrome); neurotic disorders; attention deficit disorder (ADD); subdural hematoma; normal-pressure hydrocephalus; brain tumor; head trauma (postconcussional disorder) and brain trauma (see DSM-IV, APA 1994).

The ability of a compound to inhibit PDE 4 activity can be determined using assays that are known, or it can be determined using the following assay.

PDE4 Inhibition Assay

PDE4 from human U-937 cells was used (see T. J. Torphy, et al., *J. Pharmacol. Exp. Ther.*, 1992, 263, 1195-1205). Test compound at various concentration and/or vehicle was pre-incubated with 2 µg/ml enzyme in Tris-HCl buffer pH 7.5 for 15 minutes at 25° C. The reaction was initiated by addition of 1 µM cAMP and 0.01 µM [$^3$H]-cAMP for another 20 minute incubation period and terminated at 100° C. The resulting [$^3$H]-AMP was converted to [$^3$H]-adenosine by addition of snake venom nucleotidase and separated by AG1-X2 resin. An aliquot was removed and counted to determine the amount of [$^3$H]-adenosine formed. Results were converted to percent inhibition and $IC_{50}$ determined using XLfit from IDBS (ID Business Solutions Ltd., 2 Occam Court, Surrey Research Park, Guildford, Surrey, GU2 7QB UK).

Representative compounds of the invention were tested and found to have significant PDE4 inhibition in this assay.

The ability of a compound to activate CREB can be determined using the following assay.

CREB Activation Assay

The following CRE-Luci assay is a high throughput, well-based method for identifying compounds that enhance cognition by increasing CREB pathway function. The assay enables the identification of cognitive enhancers that do not affect CREB pathway function alone, but act to increase (enhance) CREB pathway function in combination with a CREB function stimulating agent.

The assay is carried out by (a) contacting host cells (particularly cells of neural origin (e.g. human neuroblastoma SK-N-MC cells) having a luciferase gene operably linked to a CRE promoter with a test compound and a suboptimal dose of a CREB function stimulating agent (e.g., forskolin); (b) determining luciferase activity in the host cells which have been contacted with the test compound and with the CREB function stimulating agent; and (c) comparing the luciferase activity determined in step (b) with the luciferase activity in control cells which have been contacted with the CREB function stimulating agent and which have not been contacted with the test compound (i.e., control cells which have been contacted with the CREB function stimulating agent alone).

Host cells comprising luciferase gene operably linked to a CRE-promoter can be manufactured by introducing into cells a DNA construct comprising a luciferase gene operably linked to a CRE promoter. DNA constructs can be introduced into cells according to methods known in the art (e.g., transformation, direct uptake, calcium phosphate precipitation, electroporation, projectile bombardment, using liposomes). Such methods are described in more detail, for example, in Sambrooke et al., Molecular cloning: A laboratory Manual, $2^{nd}$ edition (New York: Cold Spring Harbor University Press) (1989); and Ausubel, et al., Current Protocols in Molecular Biology (New York: John Wiley & Sons) (1998).

SK-N-MC cells stably transfected with CRE-luc construct are seeded in 96-well, white assay plates (PerkinElmer) at a concentration of 20,000 cells/well in 100 µL MEM complete media. These cells are incubated in a $CO_2$ incubator under standard cell culture condition. After 18 to 24 hours of incubation, cells are treated with either a vehicle control (DMSO, Sigma), the test compounds (5 µM final concentration), or a positive control (HT-0712, 5 µM final concentration) (16 wells for each treatment) for 2 hours. Forskolin (5 µM final concentration, Sigma) is then added to 8 wells of each treatment group and an equivalent amount of DMSO is added to the other 8 wells. Six hours after forskolin addition, luciferase activity is measured by adding 25 µL of assay reagent (BriteLite kit, PerkinElmer) to each well. After incubation at room temperature for 3 minutes, luminescence is detected using a Wallac Victor5 plate reader (PerkinElmer). The transcription induction ratio is derived by normalizing the luciferase activity of the compound or positive control in the presence of forskolin over forskolin treatment alone. The compound treatment alone serves as control to determine whether compound can active CRE promoter by itself.

Representative compounds of the invention were found to increase CREB pathway function using this assay.

The ability of a compound to modulate cognitive behavior can be evaluated using the following Contextual Memory Assay.

Contextual Memory Assay: Fear Conditioning

Contextual memory is a form of Pavlovian fear conditioning in which a naïve mouse is placed into a novel chamber (context) containing distinct visual, olfactory and tactile cues. After several minutes of acclimation, the mouse receives a brief, mild electric shock to its feet. From this negative experience, the mouse will remember for months that that chamber is dangerous. When placed back into the same context at some later time after training, the mouse's natural response to danger is to "freeze," sitting stone still for many seconds. This is similar to what happens to humans when they experience fear. The percent of time during an observation period that the mouse spends frozen represents a quantitative measure (memory score) of its memory of the context.

Contextual conditioning has been extensively used to investigate the neural substrates mediating fear-motivated learning (Phillips, LeDoux, *Behav Neurosci*, 1992, 106, 274-285; Kim, et. al., *Behav Neurosci*, 1993, 107, 1093-1098; Bourtchouladze, et. al., *Learn Mem*, 1998, 5, 365-374; and Bourtchouladze et. al., *Cell*, 1994, 79, 59-68). Contextual conditioning has been also used to study the impact of various mutations on hippocampus-dependent memory (Bourtchouladze, et. al., *Learn Mem*, 1998, 5, 365-374; Bourtchouladze, et. al., *Cell*, 1994, 79, 59-68; Silva, et. al., *Curr Biol*, 1996, 6, 1509-1518; Kogan, et al., *Curr Biol*, 1997, 7, 1-11; Abel, et. al., *Cell*, 1997, 88, 615-626; and Giese, et al., *Science*, 1998, 279, 870-873); and strain and genetic background differences in mice (Logue, et al., *Behav Neurosci*, 1997, 111, 104-113; and Nguyen, et. al., *Learn Mem*, 2000, 7, 170-179). Because robust memory can be triggered with a few minutes training session, contextual conditioning has been especially useful to study biology of temporally distinct processes of short- and long-term memory (Kim, et. al., *Behav Neurosci*, 1993, 107, 1093-1098; Bourtchouladze, et. al., *Learn Mem*, 1998, 5, 365-374; Bourtchouladze, et. al., *Cell*, 1994, 79, 59-68; and Abel, et. al, *Cell*, 1997, 88, 615-626). As such, contextual conditioning is an excellent model to evaluate the role of various novel drug-compounds in hippocampus-dependent memory.

Young-adult (10-12 weeks old) C57BL/6 male mice and Sprague Dawley male rats of 250-300 g (Taconic, N.Y.) were used. Mice were group-housed (5 mice) in standard laboratory cages while rats were housed in pairs and maintained on a 12:12 light-dark cycle. The experiments were always conducted during the light phase of the cycle. With the exception of testing times, the mice had ad lib access to food and water. The experiments were conducted according with the Animal Welfare assurance #A3280-01 and animals were maintained in accordance with the animal Welfare Act and Department of Health and Human Services guide.

To assess contextual memory, a modified contextual fear conditioning task originally developed for evaluation of memory in CREB knock-out mice was used (Bourtchouladze, et. al., *Cell*, 1994, 79, 59-68). On the training day, the mouse was placed into the conditioning chamber (Med Associates, Inc., VA) for 2 minutes before the onset of unconditioned stimulus (US), 0.5 mA, of 2 sec foot shock. The US was repeated two times with a 1 min inter-trial interval between shocks. Training was performed by automated software package (Med Associates, Inc., VA). After the last training trial, the mice were left in the conditioning chamber for another 30 sec and were then placed back in their home cages. 24 hours after training, the mouse was placed into the same training chamber and contextual memory was assessed by scoring freezing behavior ('freezing' serves as memory score). Freezing was defined as the complete lack of movement in intervals of 5 seconds (Kim, et. al., *Behav Neurosci*, 1993, 107, 1093-1098; Phillips, LeDoux, *Behav Neurosci*, 1992, 106, 274-285; Bourtchouladze, et. al., *Learn Mem*, 1998, 5, 365-374; and Bourtchouladze, et. al., *Cell*, 1994, 79, 59-68; Abel, et. al., *Cell*, 1997, 88, 615-626). Total testing time lasted 3 minutes. After each experimental subject, the experimental apparatus was thoroughly cleaned with 75% ethanol, water, dried, and ventilated for a few minutes.

All experiments were designed and performed in a balanced fashion, meaning that (i) for each experimental condition (e.g. a specific dose-effect) an equal number of experimental and control mice was used; (ii) each experimental condition was replicated 2-3 independent times, and replicate days were added to generate final number of subjects. The proceeding of each experiment was filmed. In each experiment, the experimenter was unaware (blind) to the treatment of the subjects during training and testing. Data were analyzed by Student's unpaired t test using a software package (Statview 5.0.1; SAS Institute, Inc). All values in the text and figures are expressed as mean±SEM.

Compounds were dissolved in 1% DMSO/PBS and administered intraperitonially (I.P.) in a volume of 8 mL/kg 20 min before training. Control animals received vehicle alone (1% DMSO/PBS). For oral administration the compounds were dissolved in 30% DMSO/1.4% CMC. Consequently, control animals received 30% DMSO/1.4% CMC. For each training and drug-injecting procedure, an experimentally naïve group of animals were used.

To evaluate the effects of Compound 50 on contextual memory, mice were injected with Compound 50 or vehicle 20 minutes before training and trained with 2 training trials (US). Mice were than tested in the same context 24 hours after training (FIG. 1). 1 mg/kg Compound 50-injected mice froze significantly more than vehicle injected mice (32.5+3.2% vs. 22.3+3.2%; n=22 and n=20 for Compound 50 and controls, respectively; p<0.05, Student's unpaired t test). Similarly, 10 mg Compound 50-injected mice showed significantly more memory than vehicle injected mice (38.3% vs. 22.3+3.2%; n=22 and n=20, for Compound 50 and controls, respectively; p<0.005, Student's unpaired t test), while 0.1 mg/kg Compound 50 had no significant effect on contextual memory.

The ability of a compound to modulate cognitive behavior can also be evaluated using the following Object Recognition Assay.

Object Recognition Assay

Object recognition is an ethologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze, et. al., *Proc Natl Acad Sci USA*, 2003, 100, 10518-10522). Recent neuroimaging studies in humans demonstrated that memory in object recognition depends on prefrontal cortex (PFC) (Deibert, et. al., *Neurology*, 1999, 52, 1413-1417). Consistent with these findings, rats with the PFC lesions show poor working memory when they are required to discriminate between familiar and novel objects (Mitchell, Laiacona, *Behav Brain Res*, 1998, 97, 107-113). Other studies on monkeys and rodents suggest that the hippocampus is important for novel object recognition (Teng, et. al., *J. Neurosci*, 2000, 20, 3853-3863; Mumby, *Brain Res*, 2001, 127, 159-181). Hence, object recognition provides an excellent behavioral model to evaluate drug-compound effects on cognitive task associated with function of hippocampus and cortex.

Prior to initiation of training, animals were handled for 3-5 minutes for 5 days. Training and testing were performed identically for mice and rats with an exception of training apparatus dimensions (for mice: a Plexiglas box of L=48 cm; W=38 cm and H=20 cm; for rats: a Plexiglas box of L=70 cm; W=60 cm and H=35 cm). The day before training, an individual animal was placed into a training apparatus located in a dimly lit room and allowed to habituate to the environment for 15 minutes (also see Pittenger, et. al., *Neuron,* 2002, 34, 447-462; and Bourtchouladze, et. al., *Proc Natl Acad Sci USA,* 2003, 100, 10518-10522). Training was initiated 24 h hours after habituation. An animal was placed back into the training box, which contained two identical objects (e.g. a small conus-shape object), and was allowed to explore these objects. The objects were placed into the central area of the box and the spatial position of objects (left-right sides) was counterbalanced between subjects. Animals were trained for 15 minutes. To test for memory retention, animals were observed for 10 minutes 24 hours after training. A rodent was presented with two objects, one of which was used during training, and thus was 'familiar' and the other of which was novel (e.g. a small pyramid-shape object). To insure that the discrimination targets do not differ in smell, after each experimental subject, the apparatus and the objects were thoroughly cleaned with 90% ethanol, dried and ventilated for a few minutes.

The experiments were videotaped via an overhead video camera system. Types were then reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur, Aggleton, *Behav Brain Res,* 1997, 88, 181-193; and Bourtchouladze, et. al, *Proc Natl Acad Sci USA,* 2003, 100, 10518-10522). This Data was analyzed by Student's unpaired t test using a software package (Statview 5.0.1; SAS Institute, Inc). All values in the text and figures are expressed as mean±SEM.

The invention will now be illustrated by the following non-limiting examples.

LC/MS Protocol

Equipment: Waters 2695 Separations Unit, 2487 Dual Absorbance Detector, Micromass ZQ fitted with ESI Probe.

Sample Preparation: Materials dissolved in acetonitrile and diluted with equal volume water.

LC Protocol: Observed, 254 nm. Solvent system, acetonitrile (0.1% formic acid) and water (0.1% formic acid). Column, XTerra MS C-18 3.5 uM (2.1×50 mm), 30 C oven temperature. Run time, 10 min. Flow rate 0.3 ml/min.

Inlet Method:

| Time (min) | % acetonitrile (0.1% formic acid) | % water (0.1% formic acid) |
|---|---|---|
| 0 | 10 | 90 |
| 5 | 90 | 10 |
| 7 | 90 | 10 |
| 7.5 | 10 | 90 |

NMR Protocol

Analysis was carried out on a VarianMercury 300 MHz NMR. Samples were analyzed in either chloroform-D or dimethyl sulfoxide-$D_8$. For chloroform-D samples, tetramethylsilane (TMS) was used as an internal standard with the TMS resonance set to a chemical shift of 0.00 ppm for $^1H$ NMR spectra. The $^{13}C$ NMR spectra were set to the internal residual chloroform resonance at 77.23 ppm. For dimethyl sulfoxide-$D_8$, the residual central resonance peak at 2.54 ppm for $^1H$ and 39.51 for $^{13}C$ was used as reference for chemical shift assignment. DEPT experiments are expressed in the $^{13}C$ NMR listings by notation of their respective multiplicity: CH, $CH_2$, and $CH_3$.

PREPARATIVE EXAMPLES 1-20

Intermediate nitrogen containing heterocyclic diones were prepared as illustrated below.

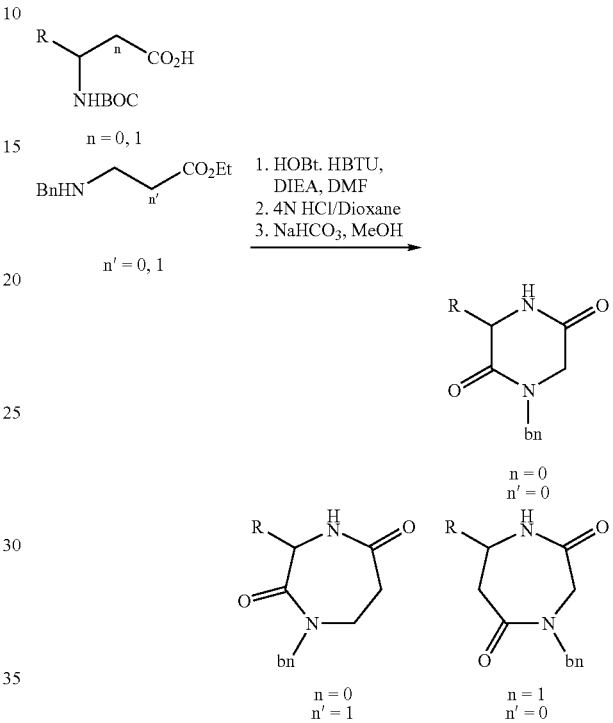

Preparative Example 1

1-Benzyl-3(S)-(2'-methylbenzyl)-piperazine-2,5-dione

A solution of Boc-2-methyl-L-phenylalanine (2.79 g, 10 mmol) in DMF (25 mL) was treated sequentially with HOBt (2.03 g, 15 mmol), DIEA (4.35 mL, 25 mmol), N-benzylglycine ethyl ester (2.03 mL, 11 mmol), and HBTU (5.69 g, 15 mmol). The resulting solution was allowed to stir for 16 hr after which time the mixture was poured onto a mixture of 1 N HCl (50 mL) and EtOAc (50 mL). The organic portion was separated and further extracted with a saturated $NaHCO_3$ solution (50 mL) follow by brine (50 mL). The organic phase was dried over $MgSO_4$, filtered and evaporated to an oil, which was purified by silica gel flash chromatography with 20% then 30% EtOAc/hexanes as eluant to afford product as a solid (4.31 g, 95%). LC/MS 7.43 min, $[M+1]^+$ 455.

The coupled product was dissolved in 4N solution of hydrogen chloride in 1,4-dioxane and stirred for 3 hr at room temperature then evaporated to dryness and placed on a vacuum pump for 24 hr. The crude deprotected material was then dissolved in MeOH (10 mL) and treated with a saturated aqueous solution of $NaHCO_3$ (~10 mL). The solution rapidly solidified and the resulting paste filtered with the aid of water and air dried to provide solid product (2.83 g, 97%). $^1H$ NMR (DMSO-$d_6$) 2.28 (s, 3H), 2.53-2.55 (m, 1H), 2.83 (d, J=17.1, 1H), 3.05 (dd, J=14.1, 5.1, 1H), 3.05 (dd, J=13.8, 5.1, 1H), 3.46 (d, J=17.1, 1H), 4.21-4.25 (m, 1H), 4.39 (d, J=14.5, 1H), 4.49 (d, J=14.5, 1H) 6.88-6.93 (m, 1H), 7.01 (d, J=7.3, 1H), 7.11-7.14 (m, 2H), 7.19-7.22 (m, 2H), 7.33-7.41 (m, 3H), 8.35 (br d, J=2.6, 1H). $^{13}$C NMR 19.3 (CH$_3$), 36.2 (CH$_2$), 48.3 (CH$_2$), 48.5 (CH$_2$), 55.7 (CH), 125.5 (CH), 126.8 (CH), 127.5 (CH), 128.2 (CH), 128.5 (CH), 130.2 (CH), 130.5 (CH), 134.1, 135.8, 136.9, 164.9, 166.0. LC/MS 3.78 min, [M+1]$^+$ 309.

Preparative Example 2

1-Benzyl-3(R)-(benzyl)-piperazine-2,5-dione

Colorless solid (88%); $^1$H NMR (DMSO-$_{d6}$) 2.69 (d, J=17.1, 1H), 2.93 (dd, J=13.6, 4.8, 1H), 3.20 (dd, J=13.6, 4.2, 1H), 3.49 (d, J=17.1, 1H), 4.22 (d, J=14.5, 1H), 4.31 (m, 1H), 4.63 (d, J=14.5, 1H), 7.11-7.25 (m, 7H), 7.32-7.38 (m, 3H), 8.379 (s, 1H). LC/MS 4.98 min, [M+1]$^+$ 295

Preparative Example 3

1-Benzyl-3(S)-(3'-methylbenzyl)-piperazine-2,5-dione

Colorless solid (100%); $^1$H NMR (DMSO-$_{d6}$) 2.23 (s, 1H), 2.53-2.55 (m, 1H), 2.78 (d, J=17.1, 1H), 2.91 (dd, J=13.4, 4.8, 1H), 3.15 (dd, J=13.4, 4.0, 1H), 3.50 (d, J=17.4, 1H), 4.24-4.29 (m, 2H), 4.59 (d, J=14.5, 1H) 6.89-6.92 (m, 1H), 7.01 (br s, 1H), 7.05-7.06 (m, 2H), 7.12-7.16 (m, 2H), 7.30-7.37 (m, 3H), 8.35 (br s, 1H). $^{13}$C NMR 20.9, 48.3, 55.5, 127.0, 127.3, 127.4, 127.9, 128.0, 128.5, 130.7, 135.5, 135.7, 137.0, 164.9, 165.4. LC/MS 4.53 min, [M+1]$^+$ 309.

Preparative Example 4

1-Benzyl-3(S)-(4'-methylbenzyl)-piperazine-2,5-dione

Colorless solid (94%); $^1$H NMR (DMSO-$_{d6}$) 2.25 (s, 3H), 2.53-2.55 (m, 1H), 2.69 (d, J=17.4, 1H), 2.89 (dd, J=13.4, 4.6, 1H), 3.15 (dd, J=13.4, 4.0, 1H), 3.49 (d, J=17.1, 1H), 4.20 (d, J=14.3, 1H), 4.28 (br t, J=4.0, 1H), 4.64 (d, J=14.5, 1H), 6.97 (m, 4H), 7.14-7.17 (m, 2H), 7.33-7.36 (m, 3H), 8.35 (br s, 1H). $^{13}$C NMR 20.6, 38.8, 48.2, 48.3, 55.6, 127.4, 128.3, 128.4, 128.6, 129.9, 132.3, 135.7, 135.7, 164.9, 165.4. LC/MS 4.01 min, [M+1]$^+$ 309.

Preparative Example 5

1-Benzyl-3(S)-(2'-methoxybenzyl)-piperazine-2,5-dione

Colorless solid (78%); $^1$H NMR (DMSO-$_{d6}$) 2.99 (dd, J=13.4, 5.9, 1H), 3.14 (obs dd, J=13.4, 5.3, 1H), 3.19 (obs d, J=17.1, 1H), 3.51 (d, J=17.1, 1H), 3.78 (s, 3H), 4.15-4.20 (m, 1H), 4.47 (s, 2H) 6.75 (t, J=7.5, 1H), 6.97 (d, J=8.1, 1H), 7.03 (dd, J=7.3, 1.5, 1H), 7.22-7.28 (m, 3H), 7.33-7.42 (m, 3H), 8.12 (d, J=2.2, 1H). LC/MS 5.02 min, [M+1]$^+$ 325.

Preparative Example 6

1-Benzyl-3(S)-(3'-methoxybenzyl)-piperazine-2,5-dione

Colorless solid (60%); $^1$H NMR (DMSO-$_{d6}$) 2.86 (d, J=17.6, 1H), 2.92 (obs dd, J=13.4, 4.6, 1H), 3.17 (dd, J=13.4, 4.2, 1H), 3.52 (d, J=17.4, 1H), 3.72 (s, 3H), 4.27 (d, J=14.7, 1H), 4.32 (m, 1H), 4.60 (d, J=14.5, 1H), 6.69 (d, J=7.5, 1H), 6.75 (m, 1H), 6.83 (dd, J=8.1, 2.4, 1H), 7.07 (d, J=7.9, 1H), 7.11-7.14 (m, 3H), 7.30-7.36 (m, 3H), 8.39 (s, 1H). LC/MS 4.95 min, [M+1]$^+$ 325.

Preparative Example 7

1-Benzyl-3(S)-(4'-methoxylbenzyl)-piperazine-2,5-dione

Colorless solid (83%); $^1$H NMR (DMSO-$_{d6}$) 2.64 (d, J=17.4, 1H), 2.84 (dd, J=13.3, 4.6, 1H), 3.13 (dd, J=13.6, 3.7, 1H), 3.49 (d, J=17.4, 1H), 3.71 (s, 3H), 4.15 (d, J=14.5, 1H), 4.25 (m, 1H), 4.69 (d, J=14.5, 1H), 6.67 (d, J=8.8, 2H), 6.97 (d, J=8.8, 2H), 7.16-7.19 (m, 2H), 7.35-7.37 (m, 3H), 8.34 (d, J=2.3, 1H). LC/MS 4.93 min, [M+1]$^+$ 325.

Preparative Example 8

1-Benzyl-3(S)-(4'-ethoxylbenzyl)-piperazine-2,5-dione

Colorless solid (90%); $^1$H NMR (DMSO-$_{d6}$) 1.33 (t, J=7.0, 1H), 2.64 (d, J=17.4, 1J), 2.84 (dd, J=13.6, 4.8, 1H), 3.12 (dd, J=13.6, 3.7, 1H), 3.48 (d, J=17.1, 1H), 3.91-3.99 (m, 2H), 4.17 (d, J=14.5, 1H), 4.24 (br s, 1H), 4.67 (d, J=14.5, 1H), 6.66 (d, J=8.6, 2H), 6.96 (d, J=8.8, 2H), 7.16-7.19 (m, 2H), 7.34-7.37 (m, 3H), 8.35 (br s, 1H). LC/MS 4.33 min, [M+1]$^+$ 339.

Preparative Example 9

1-Benzyl-3(S)-(2-phenethyl)-piperazine-2,5-dione

Colorless solid (92%); $^1$H NMR (DMSO-$_{d6}$) 2.02-2.11 (m, 2H), 2.64-2.71 (m, 2H), 3.83 (d, J=17.1, 1H), 3.95 (d, J=17.4, 1H), 4.00-4.01 (m, 1H), 4.52 (d, J=14.7, 1H), 4.63 (d, J=14.7, 1H), 7.19-7.42 (m, 10H), 8.55 (br d, J=1.8, 1H). $^{13}$C NMR 30.3, 35.0, 48.5, 49.1, 54.0, 125.9, 127.5, 127.8, 128.4, 128.6, 136.4, 141.2, 165.5, 166.3. LC/MS 4.72 min, [M+1]$^+$ 309.

Preparative Example 10

1-Benzyl-3(R)-(2-phenethyl)-piperazine-2,5-dione

Colorless solid (92%). LC/MS 5.32 min, [M+1]$^+$ 309.

Preparative Example 11

1-Benzyl-3(S)-(3-phenylpropyl)-piperazine-2,5-dione

Colorless solid (91%); $^1$H NMR (DMSO-$_{d6}$) 1.60-1.68 (m, 2H), 1.75-1.84 (m, 2H), 2.61 (t, J=7.6), 3.77 (d, J=17.3, 1H), 3.87 (d, J=17.3, 1H), 4.47 (d, J=14.9, 1H), 4.62 (d, J=14.6, 1H), 7.20-7.23 (m, 3H), 7.27-7.41 (m, 7H), 8.42 (d, J=2.3, 1H). LC/MS 5.59 min, [M+1]$^+$ 323.

Preparative Example 12

1-Benzyl-3(S)-(1'-naphthylmethyl)-piperazine-2,5-dione

Colorless solid (89%); $^1$H NMR (DMSO-$_{d6}$) 2.96 (d, J=17.1, 1H), 3.41 (d, J=17.1, 1H), 3.50-3.64 (m, 2H), 4.35 (m, 3H), 7.06-7.09 (m, 2H), 7.29-7.38 (m, 5H), 7.53-7.63 (m, 2H), 7.84-7.87 (m, 1H), 7.97 (dd, J=7.3, 2.4, 1H), 8.18 (d, J=7.5, 1H), 8.37 (d, J=2.9, 1H)). $^{13}$C NMR 36.0, 48.3, 48.4, 55.8, 124.0, 125.2, 125.6, 126.1, 127.4, 127.9, 128.5, 131.9, 132.2, 133.4, 135.8, 164.9, 165.9. LC/MS 4.72 min, [M+1]$^+$ 345.

Preparative Example 13

1-Benzyl-3(S)-(2'-naphthylmethyl)-piperazine-2,5-dione

Colorless solid (92%); $^1$H NMR (DMSO-$_{d6}$) 2.81 (d, J=17.1, 1H), 3.14 (dd, J=13.6, 4.8, 1H), 3.39 (dd, J=13.4, 4.4, 1H), 3.52 (d, J=17.4, 1H), 4.19 (d, J=14.7, 1H), 4.68 (d, J=14.5, H), 7.01-7.03 (m, 2H), 7.13-7.17 (m, 2H), 7.23 (d, J=7.3, 1H), 7.31 (dd, J=8.6, 1.5, 1H), 7.51-7.56 (m, 2H), 7.70 (s, 1H), 7.74 (d, J=8.4, 1H), 7.82-7.84 (m, 1H), 7.88-7.91 (m, 1H), 8.50 (s, 1H)). $^{13}$C NMR 39.2, 48.3, 48.3, 55.6, 125.7, 126.0, 127.3, 127.5, 127.5, 127.5, 127.9, 128.2, 128.3, 128.7, 131.9, 132.8, 133.5, 135.6, 164.7, 165.3. LC/MS 4.72 min, [M+1]$^+$ 345.

Preparative Example 14

1-Benzyl-3(S)-(4'-biphenylmethyl)-piperazine-2,5-dione

Colorless solid (99%); $^1$H NMR (DMSO-$_{d6}$) 2.78 (d, J=17.4, 1H), 2.97 (dd, J=13.4, 4.8, 1H), 3.23 (dd, J=13.2, 3.9, 1H), 3.55 (d, J=17.4, 1H), 4.18 (d, J=14.5, 1H), 4.73 (d, J=14.2, H), 7.17-7.20 (m, 4H), 7.32-7.35 (m, 2H), 7.39-7.53 (m, 4H), 7.62-7.65 (m, 2H), 8.42 (s, 1H). $^{13}$C NMR 38.7, 40.3 (methylene resonance obscured by solvent, visible in DEPT experiment), 48.3, 48.4, 55.5, 126.2, 126.4, 127.3, 127.5, 128.4, 128.4, 130.6, 134.8, 135.7, 138.4, 139.6, 164.9, 165.4. LC/MS 5.39 min, [M+1]$^+$ 371.

Preparative Example 15

1-Benzyl-3(S)-(diphenylmethyl)-piperazine-2,5-dione

Colorless solid (99%); $^1$H NMR (DMSO-$_{d6}$) 3.02 (d, J=17.1, 1H), 3.51 (dd, J=17.4, 4.8, 1H), 4.20 (d, J=14.5, 1H), 4.60 (s, 1H), 4.61 (d, J=4.6, 1H), 4.80-4.83 (m, 1H), 7.12-7.16 (m, 3H), 7.22-7.38 (m, 12H). $^{13}$C NMR 49.3, 49.4, 55.4, 59.0, 127.3, 127.5, 128.2, 128.9, 128.9, 129.2, 129.3, 130.1, 136.6, 140.4, 141.1, 166.0, 166.6. LC/MS 5.28 min, [M+1]$^+$ 371.

Preparative Example 16

1-Benzyl-3(S)-(cyclohexylmethyl)-piperazine-2,5-dione

Colorless solid (93%); $^1$H NMR (DMSO-$_{d6}$) 0.84-0.99 (m, 2H), 1.12-1.24 (m, 3H), 1.46-1.80 (m, 8H), 3.75 (d, J=17.1, 1H), 3.93 (obs m, 1H), 3.94 (d, J=17.1, 1H), 4.49 (d, J=14.7, 1H), 4.60 (d, J=14.7, 1H), 7.27-7.42 (m, 5H), 8.46 (s, 1H). $^{13}$C NMR 25.6, 25.8, 26.0, 31.9, 32.8, 33.2, 40.9, 48.4, 49.0, 52.5, 127.4, 127.8, 128.6, 136.4, 165.4, 167.0. LC/MS 4.84 min, [M+1]$^+$ 301.

Preparative Example 17

Tetrahydro-1,3-bis(phenylmethyl)-(3S)-1H-1,4-Diazepine-2,5-dione

CAS [612844-06-1]; Colorless solid (64%); $^1$H NMR (DMSO-$_{d6}$) 2.15-2.27 (m, 1H), 2.43-2.51 (m, 1H), 2.84 (dd, J=14.3, 7.7, 1H), 3.11-3.21 (m, 2H), 4.00-4.10 (m, 1H), 4.50 (d, J=14.9, 1H), 4.58 (d, J=14.7, 1H), 4.77-4.82 (m, 1H), 7.16-7.53 (m, 10H). $^{13}$C NMR 34.8, 35.3, 42.1, 49.4, 52.8, 126.2, 127.2, 127.7, 128.1, 128.5, 129.4, 137.9, 138.2, 170.7, 170.9. LC/MS 5.30 min, [M+1]$^+$ 309.

Preparative Example 18

Tetrahydro-1,3-bis(phenylmethyl)-(3R)-1H-1,4-Diazepine-2,5-dione

Colorless solid (57%). LC/MS 5.30 min, [M+1]$^+$ 309.

Preparative Example 19

Tetrahydro-1,5-bis(phenylmethyl)-(5S)-1H-1,4-Diazepine-3,7-dione

Colorless solid (31%); $^1$H NMR (DMSO-$_{d6}$) 2.64-2.81 (m, 3H), 2.94 (dd, J=13.2, 4.4, 1H), 3.71-3.78 (m, 1H), 4.06 (s, 2H), 4.59 (s, 2H), 7.27-7.40 (m, 10H), 7.78 (d, J=2.2, 1H). $^{13}$C NMR 37.4, 42.7, 50.9, 52.7, 53.3, 127.2, 127.9, 128.2, 129.1, 129.2, 130.3, 137.9, 138.3, 168.8, 171.2. LC/MS 5.14 min, [M+1]$^+$ 309.

Preparative Example 20

Tetrahydro-1,5-bis(phenylmethyl)-(5R)-1H-1,4-Diazepine-3,7-dione

Colorless solid (32%). LC/MS 5.14 min, [M+1]$^+$ 309.

PREPARATIVE EXAMPLES 21-42

As illustrated below, the dione heterocycles were reduced to provide the nitrogen containing heterocycles.

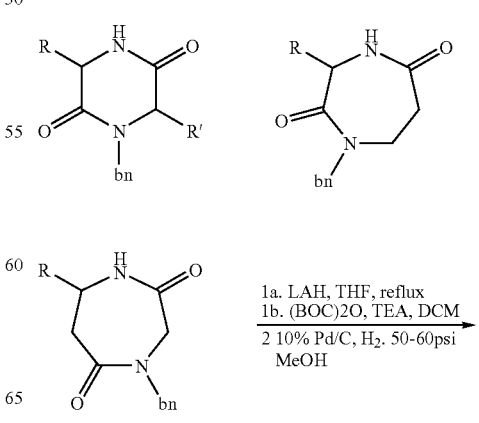

1a. LAH, THF, reflux
1b. (BOC)2O, TEA, DCM
2 10% Pd/C, H$_2$, 50-60psi MeOH

-continued

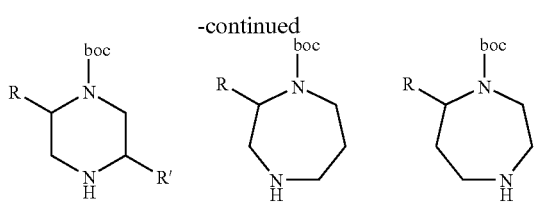

Preparative Example 21

2(S)-N1 BOC-2-(2'-methylbenzyl)piperazine

1-Benzyl-3(S)-(2-methylbenzyl)-piperazine-2,5-dione (617 mg, 2 mmol) in THF (10 mL) was treated with a 1N THF solution of LAH and heated at reflux for 6 h. The reaction was then cooled to room temperature and quenched dropwise with a 15% aqueous NaOH solution (0.5 mL) followed by water (1 mL). The resulting mixture was treated with a small amount of $MgSO_4$ and filtered through a pad of Celite® with the aid of EtOAc. The organic filtrate was then evaporated to an oil, dissolved in $CH_2Cl_2$ (5 mL), and treated with TEA (560 uL, 4 mmol) and BOC anhydride (640 mg, 3 mmol). The reaction was stirred for 3 h after which time and additional portion of $CH_2Cl_2$ (10 mL) was added and the solution washed with a saturated aqueous solution of $NH_4Cl$ (15 mL) followed by brine (2×10 mL). The organic portion was dried over $MgSO_4$, filtered and evaporated to an oil which was purified by silica gel flash chromatography with 15% EtOAc/hexanes as eluant to afford product as a colorless waxy solid (615 mg, 81%). LC/MS 5.44 min, $[M+1]^+$ 381.

The N1-BOC N-4-benzylated solid (1.2 g, 3.15 mmol) was dissolved in MeOH (60 mL) and purged with nitrogen for 3 min followed by addition of 10% palladium-on-carbon (50% water content, 500 mg). The reaction mixture was hydrogenated at ~50-60 psi hydrogen for 6 h after which time the mixture was filtered through a pad of Celite®. The organic filtrate was evaporated and dissolved in MeOH (10 mL) and filtered through a nylon syringe filter (0.45 micron, 13 mm) to remove traces of palladium-on-carbon. The organic filtrate was again evaporated to afford a clear colorless oil (875 mg, 96%). $^1$H NMR ($CDCl_3$) 1.33 (s, 9H), 2.39 (s, 3H), 2.67-2.91 (m, 4H), 2.93-3.22 (m, 3H), 3.95 (br d, J=12.5, 1H), 4.21 (br t, 1H), 7.09-7.16 (m, 4H). $^{13}$C NMR 19.7 ($CH_3$), 28.5 ($CH_3$), 32.7 ($CH_2$), 33.2 ($CH_2$), 46.3 ($CH_2$), 47.6 ($CH_2$), 51.5 (CH), 79.7, 126.1 (CH), 126.6 (CH), 126.9, 130.4 (CH), 130.5 (CH), 136.9, 137.5. LC/MS 4.09 min, $[M+1]^+$ 291.

Preparative Example 22

2(R)-N1 BOC-2-(benzyl)-piperazine

Colorless waxy solid (89%, 96%); LC/MS 3.90 min, $[M+1]^+$ 277.

Preparative Example 23

2(S)-N1 BOC-2-(3'-methylbenzyl)-piperazine

Colorless oil (84%, 92%); LC/MS 4.14 min, $[M+1]^+$ 291.

Preparative Example 24

2(S)-N1 BOC-2-(4'-methylbenzyl)-piperazine

Colorless oil (86%, 94%); LC/MS 4.10 min, $[M+1]^+$ 291.

Preparative Example 25

2(S)-N1 BOC-2-(2'-methoxylbenzyl)-piperazine

Colorless oil (83%, 94%); LC/MS 3.92 min, $[M+1]^+$ 307.

Preparative Example 26

2(S)-N1 BOC-2-(3'-methoxylbenzyl)-piperazine

Colorless oil (47%, 83%); LC/MS 3.84 min, $[M+1]^+$ 307.

Preparative Example 27

2(S)-N1 BOC-2-(4'-methoxylbenzyl)-piperazine

Colorless oil (85%, 88%); LC/MS 3.74 min, $[M+1]^+$ 307.

Preparative Example 28

2(S)-N1 BOC-2-(4'-ethoxylbenzyl)-piperazine

Colorless oil (82%, 86%); LC/MS 4.41 min, $[M+1]^+$ 321.

Preparative Example 29

2(S)-N1 BOC-2-(2-phenethyl)-piperazine

Colorless oil (83%, 96%); LC/MS 4.13 min, $[M+1]^+$ 291.

Preparative Example 30

2(R)-N1 BOC-2-(2-phenethyl)-piperazine

Colorless oil (85%, 96%); LC/MS 4.14 min, $[M+1]^+$ 291.

Preparative Example 31

2(S)-N1 BOC-2-(3-phenylpropyl)-piperazine

Colorless oil (97%, 89%); LC/MS 4.32 min, $[M+1]^+$ 305.

Preparative Example 32

2(S)-N1 BOC-2-(1'-naphthylmethyl)-piperazine

Colorless waxy solid (84%, 90%); LC/MS 4.35 min, $[M+1]^+$ 327.

Preparative Example 33

2(S)-N1 BOC-2-(2'-naphthylmethyl)-piperazine

Colorless oil (73%, 98%); LC/MS 4.39 min, $[M+1]^+$ 327.

Preparative Example 34

2(S)-N1 BOC-2-(4'-biphenylmethyl)-piperazine

Colorless waxy solid (66%, 99%); LC/MS 4.68 min, $[M+1]^+$ 353.

Preparative Example 35

2(S)-N1 BOC-2-(diphenylmethyl)-piperazine

Colorless oil (35%, 92%); LC/MS 4.40 min, $[M+1]^+$ 353.

Preparative Example 36

2(S)-N1 BOC-2-(cyclohexylmethyl)-piperazine

Colorless oil (87%, 89%); LC/MS 4.43 min, $[M+1]^+$ 283.

Preparative Example 37

(S)-2-Benzyl-[1,4]diazepane-1-carboxylic acid tert-butyl ester

Colorless oil (75%, 93%); LC/MS 3.98 min, [M+1]+ 291.

Preparative Example 38

(R)-2-Benzyl-[1,4]diazepane-1-carboxylic acid tert-butyl ester

Colorless oil (65%, 92%); LC/MS 3.95 min, [M+1]+ 291.

Preparative Example 39

(S)-7-Benzyl-[1,4]diazepane-1-carboxylic acid tert-butyl ester

Colorless oil (73%, 88%); LC/MS 4.57 min, [M+1]+ 291.

Preparative Example 40

(R)-7-Benzyl-[1,4]diazepane-1-carboxylic acid tert-butyl ester

Colorless oil (71%, 88%); LC/MS 4.57 min, [M+1]+ 291.

Preparative Example 41

(2S,5S)-2-Benzyl-5-methyl-piperazine-1-carboxylic acid tert-butyl ester

Prepared from (3S,6S)-6-methyl-, 1,3-bis(phenylmethyl)-2,5-piperazinedione (CAS [561303-33-1]) Colorless oil (66%, 92%); LC/MS 4.26 min, [M+1]+ 291.

Preparative Example 42

(2S,5R)-2-Benzyl-5-methyl-piperazine-1-carboxylic acid tert-butyl ester

Prepared from (3S,6R)-6-methyl-, 1,3-bis(phenylmethyl)-2,5-piperazinedione (CAS [850036-85-0]) Colorless oil (84%, 89%); LC/MS 4.46 min, [M+1]+ 291.

PREPARATIVE EXAMPLES 43-48

Preparative Example 43

(R)-2-benzylmorpholine

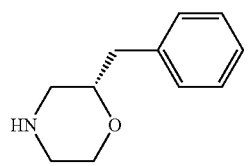

The title compound was prepared from (S)-(2,3-epoxypropyl)benzene by the method of D'Arrigo, Lattanzio, Fantoni and Servi in *Tetrahedron: Asymmetry,* 1998, 9, 4021-4026.

Preparative Example 44

6R and 6S-(phenylmethyl)piperazinone

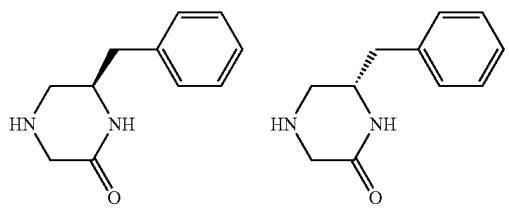

The title compound (6R)-isomer was prepared from N-Cbz-D-phenylalinal by the method of DeLucca in US2003/0144277 A1 describing the preparation of 6S-(phenylmethyl)piperazinone (CAS [503186-95-6]) from N-Cbz-L-phenylalanal. LC/MS 5.40 and 5.34 min, [M+1]+ 191 and 191.

Preparative Example 45

4-bromo-7-methoxy-spiro[benzofuran-2(3H), 1'-cyclopentane](CAS [185244-55-7])

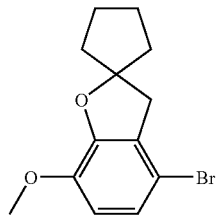

The title compound was prepared from 5-bromo-2-methoxybenzaldehyde by the method of Van der Mey, Margaretha; et. al., *Journal of Medicinal Chemistry* 2001, 44, 2523-2535.

Preparative Example 46

6-Bromo-1-cyclopentyl-3-methyl-1H-indazole

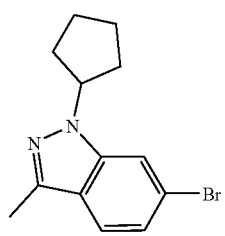

A solution of 4-bromo-2-fluoro-N-methoxy-N-methyl-benzamide (CAS [801303-33-3]) (13.1 g, 50.0 mmol) in THF (50 mL) at −78 C was treated with a 3 M solution of methyl magnesium bromide in diethyl ether (16.7 mL, 50 mmol) and allowed to warm with stirring to 0 C over a 2-3 h period, after which time the reaction mixture was quenched with a half saturated aqueous solution of NH₄Cl (100 mL) and EtOAc (200 mL). The mixture was separated and the organic component, washed with brine (2×50 mL), dried over MgSO₄, filtered, and evaporated to an oil which was purified by silica gel flash chromatography with 5% EtOAc/hexanes as eluant to afford 1-(4-bromo-2-fluorophenyl)-ethanone as a liquid (9.25 g, 85%). The ethanone (2.17 g, 10 mmol) was then dissolved in ethanol (25 mL), treated with hydrazine hydrate (535 uL, 11 mmol), and heated at reflux for 8 h. The reaction mixture was then evaporated and purified by silica gel flash chromatography with 30% then 60% EtOAc/hexanes as eluant to afford the hydrazone as a solid (2.29 g, 99%). The hydrazone (3.69 g, 16 mmol) was then treated with ethylene glycol (25 mL) and heated at 165° C. for 6 h after which time the cooled reaction mixture was poured onto water (100 mL). The aqueous mixture was neutralized, with rapid stirring, using a small amount of an aqueous saturated solution of NaHCO₃ to afford a pale yellow precipitate. The solids were filtered, washed with water, and air dried to afford cyclized indazole product (2.62 g, 78%). The indazole (2.32 g, 11 mmol) was then dissolved in anhydrous DMF (50 mL) and treated with a 60% dispersion of sodium hydride in mineral oil (420 mg, 10.5 mmol). After 30 min of stirring, cyclopentyl bromide (1.53 mL, 14.3 mmol) was added and the reaction stirred for 24 h. The reaction mixture was quenched by pouring onto water (500 mL) which was neutralized with a small portion of a 1 N aqueous HCl solution and extracted with EtOAc (2×200 mL, then 100 mL). The combined organic extracts were dried over MgSO₄, filtered, and evaporated to an oil, which was purified by silica gel flash chromatography with 25% then 80% EtOAc/hexanes as eluant to afford product as a clear yellow tinted oil (1.65 g, 54%). ¹H NMR (CDCl₃) 1.68-1.78 (m, 2H), 1.93-2.01 (m, 2H), 2.08-2.16 (m, 4H), 2.54 (s, 3H), 4.77-4.87 (m, 1H), 7.18 (dd, J=8.4, 1.5, 1H), 7.32 (dd, J=8.4, 0.7, 1H), 7.55 (d, J=1.5, 1H). ¹³C NMR 12.1 (CH₃), 24.7 (CH₂), 32.2 (CH₂), 59.5 (CH), 112.2 (CH), 120.5, 121.8 (CH), 122.5, 123.2 (CH), 141.1, 141.4. LC/MS 7.71 min, [M+1]⁺ 281.

Preparative Example 47

6-Bromo-1-cyclopentyl-3-ethyl-1H-indazole, CAS [199172-02-6]

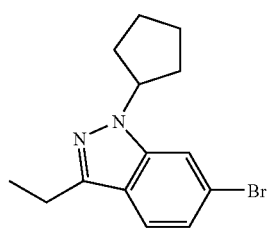

The title compound was prepared by the method outlined for Preparative Example 46 using a 25% wt THF solution of ethyl magnesium bromide and stirring the resulting solution for 24 h at 0 C in lieu of methyl magnesium bromide and a 2-3 h period at 0° C. LC/MS 8.14 min, [M+1]⁺ 295.

Preparative Example 48

2(S)-N1 BOC-2-(benzyl)-piperazine CAS [169447-86-3], 2(R)-N1 BOC-2-(phenyl)-piperazine CAS [859518-32-4], 2(S)-N1 BOC-2-(isobutyl)-piperazine, 2(R)-N1 BOC-2-(isopropyl)-piperazine, and 2(R)-N1 BOC-2-(3-indolylmethyl)-piperazine were purchased from CNH Technologies, Inc (Woburn, Mass., USA).

EXAMPLES 1-73

The following compounds of the invention were prepared as illustrated below.

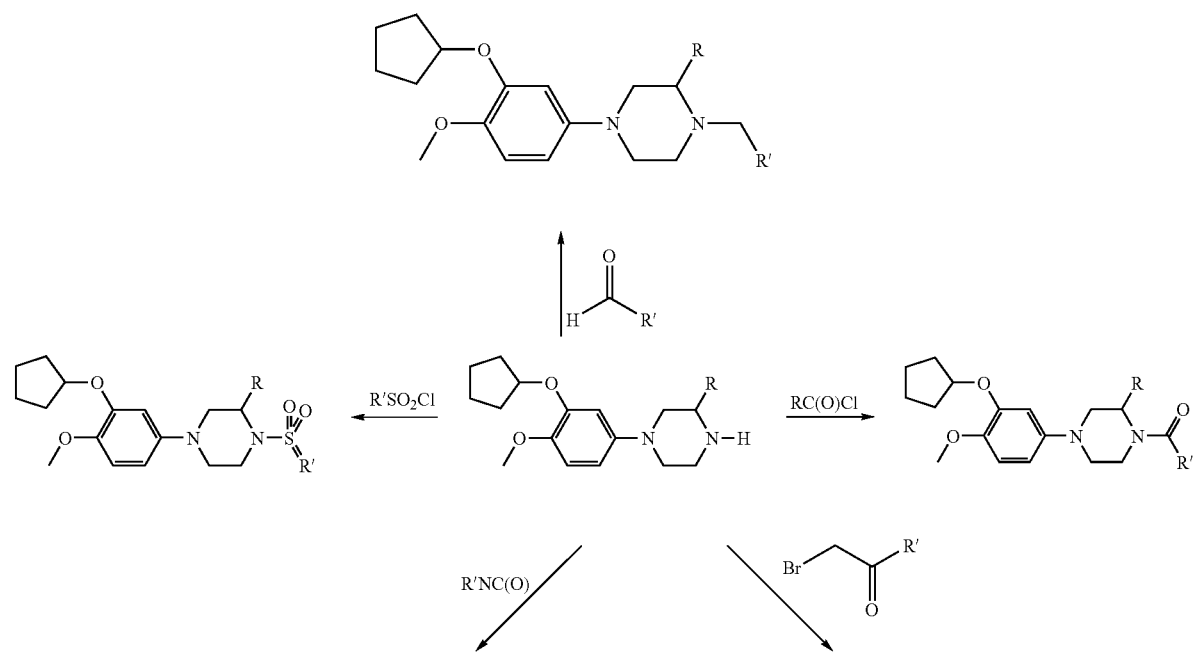

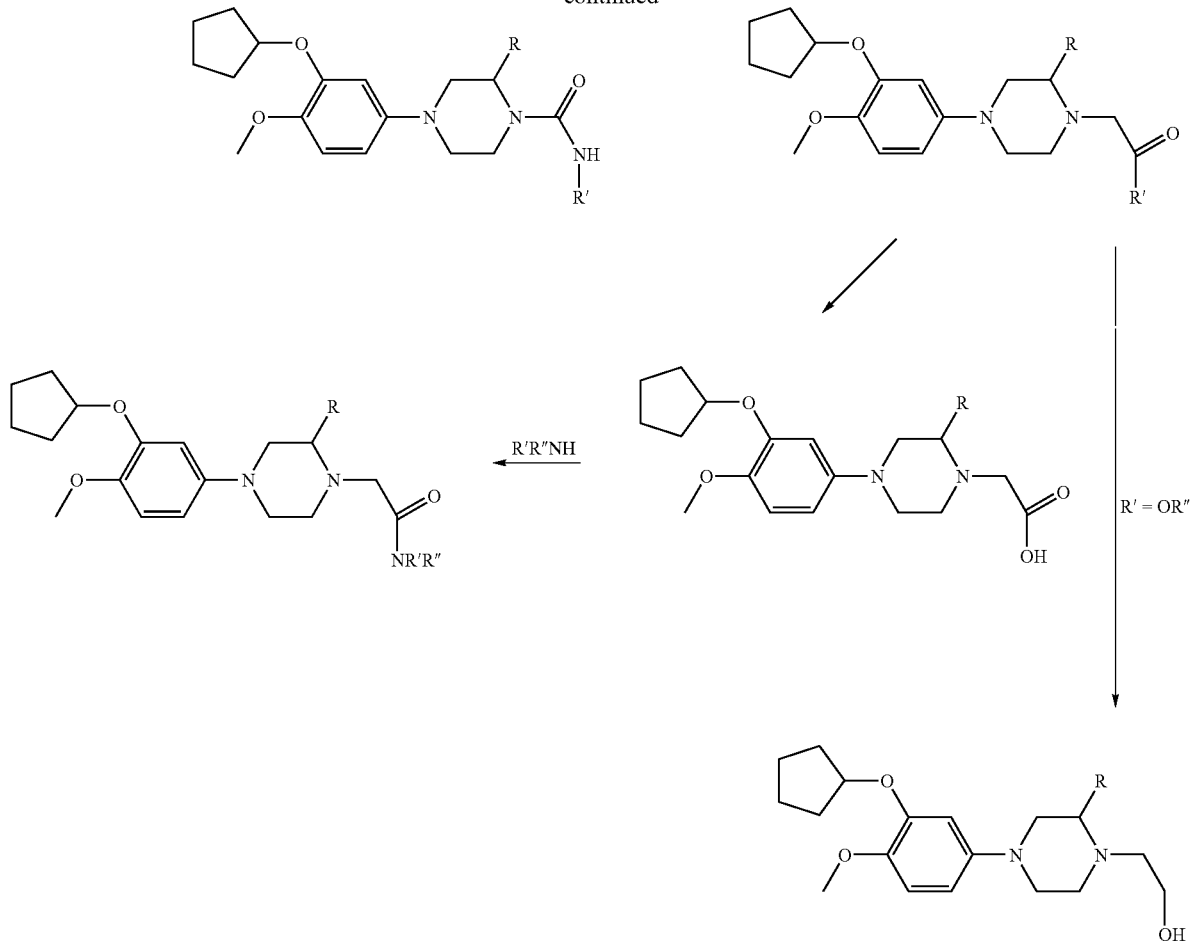

Example 1

Preparation of Compound 49, (S)-1-(3-Cyclopentyloxy-4-methoxy-phenyl)-3-(2-methyl-benzyl)-piperazine

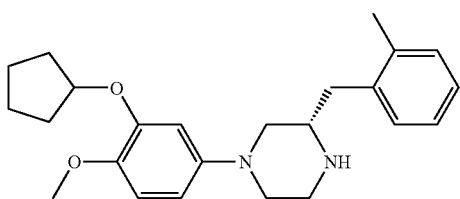

A solution of 2(S)-N1 BOC-2-(2'-methylbenzyl)piperazine (290 mg, 1.0 mmol) in anhydrous toluene (2 mL) was treated with 3-(cyclopentoxy)-4-methoxy-bromobenzene (271 mg, 1.0 mmol), sodium tert-butoxide (96 mg, 1.0 mmol), 2-dicyclohexylphosphino-2'-(N,N-dimethylamino)biphenyl (56 mg, 0.06 mmol), and tris(dibenzylideneacetone) dipalladium (14 mg, 0.015 mol). The resulting mixture was heated under nitrogen atmosphere at 100-105° C. for 5 h. The crude reaction mixture was then diluted with EtOAc (10 mL), washed with water (10 mL) followed by a saturated aqueous $NaHCO_3$ solution (10 mL), and brine (10 mL). The organic portion was then dried over $MgSO_4$, filtered and evaporated to an oil, which was purified by silica gel flash chromatography with 15% EtOAc/hexanes as eluant to afford product as an oil (215 mg, 45%). LC/MS 8.63 min, [M+1]$^+$ 481.

The purified coupled product (215 mg, 0.447 mmol) was then treated with a 4 N solution of hydrogen chloride in 1,4-dioxane and stirred for 2 h. The reaction was then evaporated to a colorless solid, suspended in EtOAc (10 mL), and washed with a saturated aqueous $K_2CO_3$ solution (3 mL) followed by brine (3 mL). The organic portion was then dried over $MgSO_4$, filtered, and evaporated to a burgundy colored oil (127 mg, 75%). $^1$H NMR (CDCl$_3$) 1.57-1.61 (m, 2H), 1.79-1.92 (m, 6H), 2.36 (s, 3H), 2.49-2.56 (m, 1H), 2.70-2.87 (m, 2H), 2.96 (td, J=11.2, 2.9, 1H), 3.08-3.16 (m, 2H), 3.35-3.39 (m, 2H), 3.78 (s, 3H), 4.71-4.74 (m, 1H), 6.43 (dd, 8.7, 2.6, 1H), 6.53 (d, J=2.9, 1H) 6.78 (d, J=8.8, 1H), 7.11-7.26 (m, 4H). $^{13}$C NMR 19.8 (CH$_3$), 24.2 (CH$_2$), 32.97 (CH$_2$), 37.9 (CH$_2$), 46.0 (CH$_2$), 51.3 (CH$_2$), 55.3 (CH), 56.8 (CH$_3$), 56.8 (CH$_2$), 80.6, (CH), 106.8 (CH), 108.6 (CH), 113.3 (CH), 126.1 (CH), 126.8 (CH), 130.2 (CH), 130.7 (CH), 136.4, 136.7, 144.8, 146.5, 148.4. LC/MS 5.03 min, [M+1]$^+$ 381.

Example 2

Preparation of Compound 50, (S)-3-Benzyl-1-(3-cyclopentyloxy-4-methoxy-phenyl)-piperazine

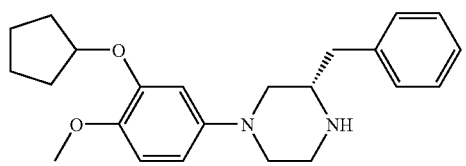

The title compound was prepared by the method outlined for Example 1 using 2(S)-N1 BOC-2-(benzyl)-piperazine CAS [169447-86-3] as amine component. Oils (68 and 90%). LC/MS 8.46 and 5.05 min, [M+1]$^+$ 467 and 367.

Example 3

Preparation of Compound 51, (2S,5S)-5-Benzyl-1-(3-cyclopentyloxy-4-methoxy-phenyl)-2-methyl-piperazine

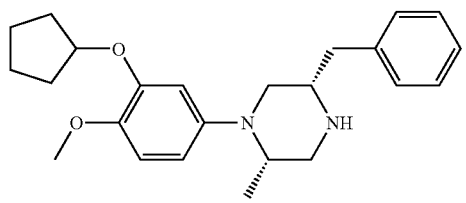

Prepared by the method outlined for Example 1 using (2S,5S)-2-Benzyl-5-methyl-piperazine-1-carboxylic acid tert-butyl ester as piperazine component. Foam and oil (33 and 96%). LC/MS 8.48 and 5.06 min, [M+1]$^+$ 481 and 381.

Example 4

Preparation of Compound 52, (2R,5S)-5-Benzyl-1-(3-cyclopentyloxy-4-methoxy-phenyl)-2-methyl-piperazine

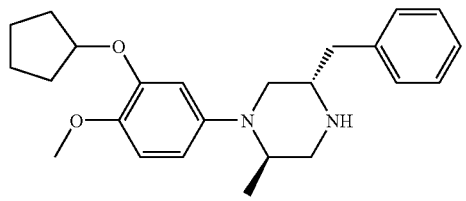

Prepared by the method outlined for Example 1 using (2S,5R)-2-Benzyl-5-methyl-piperazine-1-carboxylic acid tert-butyl ester as piperazine component. Foam and oil (61 and 86%). LC/MS 8.57 and 5.03 min, [M+1]$^+$ 481 and 381.

Example 5

Preparation of Compound 53, (R)-6-Benzyl-4-(3-cyclopentyloxy-4-methoxy-phenyl)-piperazin-2-one

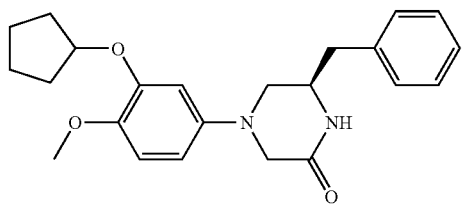

Prepared by the coupling method outlined for Example 1 using 6R-(phenylmethyl)piperazinone as amine component to afford coupled product as a colorless solid (10%). $^1$H NMR (CDCl$_3$) 1.59-1.62 (m, 2H), 1.77-1.90 (m, 6H), 2.82 (dd, J=13.4, 8.1, 1H), 2.98 (dd, J=13.6, 6.4, 1H), 3.07 (dd, J=12.5, 7.0, 1H), 3.44 (dd, J=12.5, 3.7, 1H), 3.77 (obs dd, 1H), 3.80 (s, 3H), 4.70-4.74 (m, 1H), 6.25 (br s, 1H), 6.39 (dd, 8.6, 2.6, 1H), 6.48 (d, J=2.6, 1H), 6.80 (d, J=8.8, 1H), 7.20-7.38 (m, 5H). LC/MS 6.26, [M+1]$^+$ 381.

Example 6

Preparation of Compound 54, (S)-6-Benzyl-4-(3-cyclopentyloxy-4-methoxy-phenyl)-piperazin-2-one

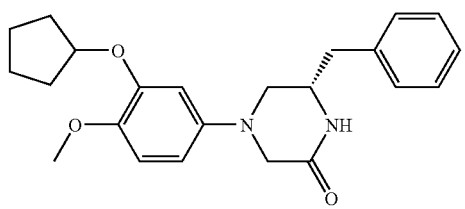

Prepared by the coupling method outlined in Example 1, using 6S-(phenylmethyl)piperazinone (CAS [503186-95-6]) as the amine component. Colorless solid (11%). LC/MS 6.39, [M+1]$^+$ 381.

Example 7

Preparation of Compound 55, (R)-3-Benzyl-1-(3-cyclopentyloxy-4-methoxy-phenyl)-piperazine

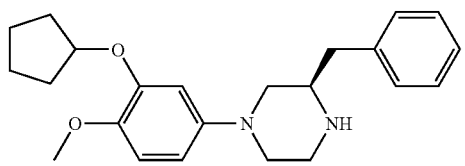

(R)-6-Benzyl-4-(3-cyclopentyloxy-4-methoxy-phenyl)-piperazin-2-one (Compound 53) (365 mg, 0.959 mmol) was dissolved in THF (10 mL), cooled to 0° C., and treated with solid lithium aluminum hydride (73 mg, 1.92 mmol). The reaction mixture was heated at 60° C. for 3 hr then cooled to 0° C. and quenched with EtOAc (2 mL) and a 1 N aqueous solution of NaOH (2 mL). The reaction was filtered with the aid of EtOAc, dried over MgSO₄, filtered, and evaporated to an oil, which was purified by silica gel flash chromatography with 5% MeOH/CH$_2$Cl$_2$ as eluant to afford product as a brown colored oil (228 mg, 65%). LC/MS 5.12 min, [M+1]$^+$ 367.

Example 8

Preparation of Compound 56, (S)-1-(3-Cyclopentyloxy-4-methoxy-phenyl)-3-(3-methyl-benzyl)-piperazine

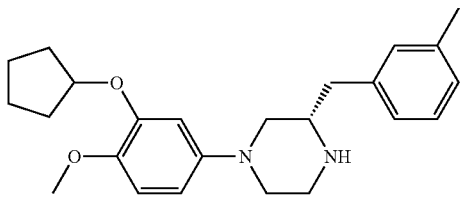

Prepared by the method outlined for Example 1 using 2(S)-N1 BOC-2-(3'methylbenzyl)-piperazine as piperazine component. Oils (38 and 92%). LC/MS 8.67 and 5.18 min, [M+1]$^+$ 481 and 381.

Example 9

Preparation of Compound 57, (S)-1-(3-Cyclopentyloxy-4-methoxy-phenyl)-3-(4-methyl-benzyl)-piperazine

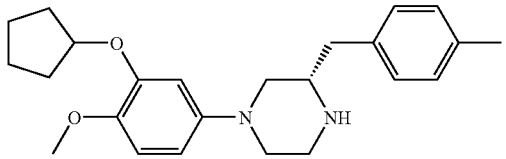

Prepared by the method outlined for Example 1 using 2(S)-N1 BOC-2-(4'-methylbenzyl)-piperazine as piperazine component. Oils (34 and 88%). LC/MS 8.68 and 5.07 min, [M+1]$^+$ 481 and 381.

Example 10

Preparation of Compound 58, (S)-1-(3-Cyclopentyloxy-4-methoxy-phenyl)-3-(2-methoxy-benzyl)-piperazine

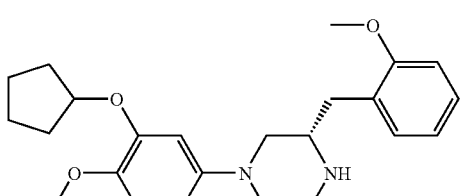

Prepared by the method outlined for Example 1 using 2(S)-N1 BOC-2-(2'-methoxybenzyl)-piperazine as piperazine component. Oils (56 and 80%). LC/MS 8.29 and 5.03 min, [M+1]$^+$ 497 and 397.

Example 11

Preparation of Compound 59, (S)-1-(3-Cyclopentyloxy-4-methoxy-phenyl)-3-(3-methoxy-benzyl)-piperazine

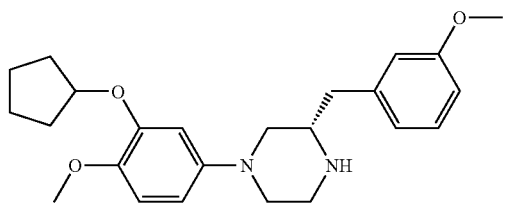

Prepared by the method outlined for Example 1 using (S)-N1 BOC-2-(3'-methoxybenzyl)-piperazine as piperazine component. Oils (42 and 92%). LC/MS 8.19 and 4.83 min, [M+1]$^+$ 497 and 397.

Example 12

Preparation of Compound 60, (S)-1-(3-Cyclopentyloxy-4-methoxy-phenyl)-3-(4-methoxy-benzyl)-piperazine

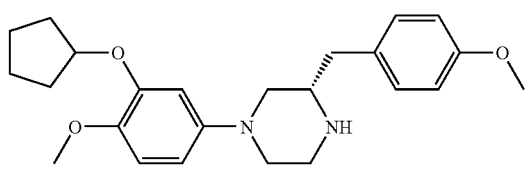

Prepared by the method outlined for Example 1 using (S)-N1 BOC-2-(4'-methoxybenzyl)-piperazine as piperazine component. Oils (64 and 85%). LC/MS 8.15 and 4.81 min, [M+1]$^+$ 497 and 397.

Example 13

Preparation of Compound 61, (S)-1-(3-Cyclopentyloxy-4-methoxy-phenyl)-3-(4-ethoxy-benzyl)-piperazine

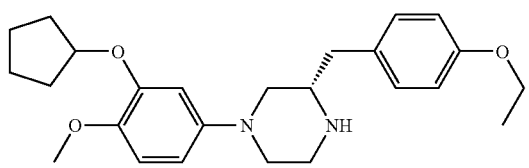

Prepared by the method outlined for Example 1 using (S)-N1 BOC-2-(4'-ethoxybenzyl)-piperazine as piperazine component. Oils (67 and 75%). LC/MS 8.44 and 4.96 min, [M+1]$^+$ 511 and 411.

Example 14

Preparation of Compound 62, (S)-1-(3-Cyclopenty-loxy-4-methoxy-phenyl)-3-phenethyl-piperazine

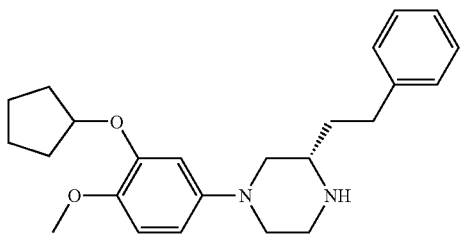

Prepared by the method outlined for Example 1 using 2(S)-N1 BOC-2-(2-phenethyl)-piperazine as piperazine component. Oils (44 and 91%). LC/MS 8.49 and 4.91 min, [M+1]$^+$ 481 and 381.

Example 15

Preparation of Compound 63, (R)-1-(3-Cyclopenty-loxy-4-methoxy-phenyl)-3-phenethyl-piperazine

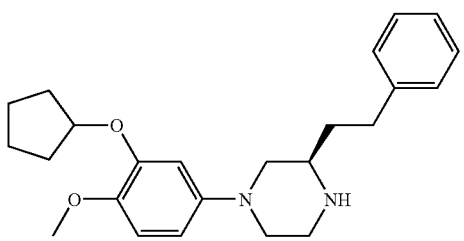

Prepared by the method outlined for Example 1 using 2(R)-N1 BOC-2-(2-phenethyl)-piperazine as piperazine component. Oils (51 and 86%). LC/MS 8.49 and 4.96 min, [M+1]$^+$ 481 and 381.

Example 16

Preparation of Compound 64, (S)-1-(3-Cyclopenty-loxy-4-methoxy-phenyl)-3-(3-phenyl-propyl)-piperazine

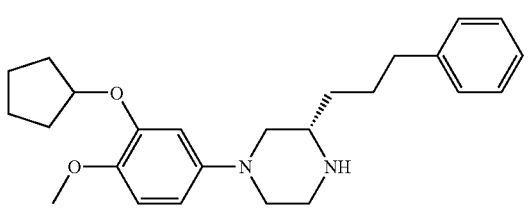

Prepared by the method outlined for Example 1 using 2(S)-N1 BOC-2-(3-phenylpropyl)-piperazine as piperazine component. Oils (38 and 91%). LC/MS 8.71 and 5.22 min, [M+1]$^+$ 495 and 395.

Example 17

Preparation of Compound 65, (S)-1-(3-Cyclopenty-loxy-4-methoxy-phenyl)-naphthalen-1-ylmethyl-piperazine

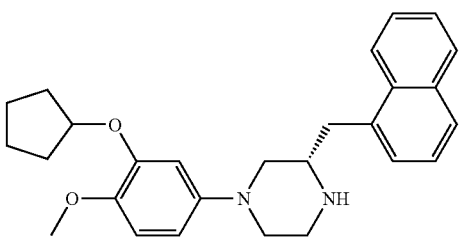

Prepared by the method outlined for Example 1 using 2(S)-N1 BOC-2-(1'-naphthylmethyl)-piperazine as piperazine component. Oils (42 and 96%). LC/MS 8.81 and 5.30 min, [M+1]$^+$ 517 and 417.

Example 18

Preparation of Compound 66, (S)-1-(3-Cyclopenty-loxy-4-methoxy-phenyl)-3-naphthalen-2-ylmethyl-piperazine

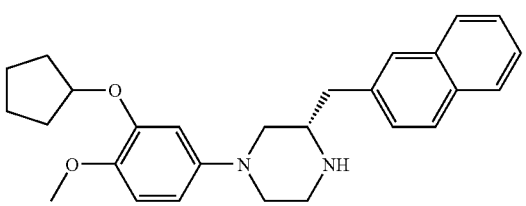

Prepared by the method outlined for Example 1 using 2(S)-N1 BOC-2-(2'-naphthylmethyl)-piperazine as piperazine component. Oils (43 and 89%). LC/MS 8.78 and 5.29 min, [M+1]$^+$ 517 and 417.

Example 19

Preparation of Compound 67, (S)-3-Biphenyl-4-ylmethyl-1-(3-cyclopentyloxy-4-methoxy-phenyl)-piperazine

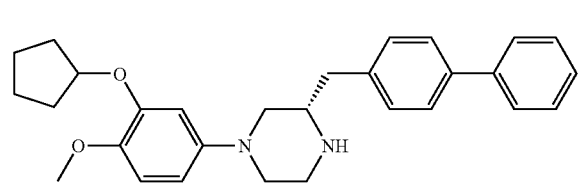

Prepared by the method outlined for Example 1 using 2(S)-N1 BOC-2-(4'-biphenylmethyl)-piperazine as piperazine component. Oils (59 and 94%). LC/MS 9.03 and 5.52 min, [M+1]$^+$ 543 and 443.

Example 20

Preparation of Compound 68, (S)-3-Benzhydryl-1-(3-cyclopentyloxy-4-methoxy-phenyl)-piperazine

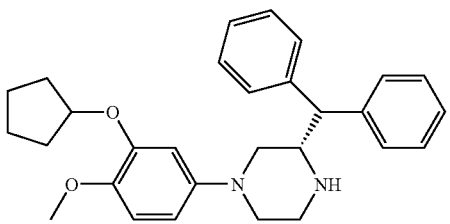

Prepared by the method outlined for Example 1 using 2(S)-N1 BOC-2-(diphenylmethyl)-piperazine as piperazine component. Oils (28 and 100%). LC/MS 8.58 and 5.39 min, [M+1]$^+$ 543 and 443.

Example 21

Preparation of Compound 69, (R)-1-(3-Cyclopentyloxy-4-methoxy-phenyl)-3-phenyl-piperazine

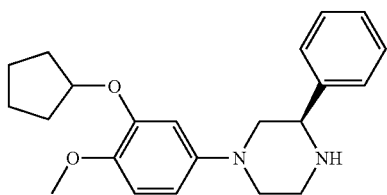

Prepared by the method outlined for Example 1 using 2(R)-N1 BOC-2-(phenyl)-piperazine as piperazine component. Foam and oil (66 and 86%). LC/MS 8.09 and 4.78 min, [M+1]$^+$ 453 and 353.

Example 22

Preparation of Compound 70, (S)-1-(3-Cyclopentyloxy-4-methoxy-phenyl)-3-isopropyl-piperazine

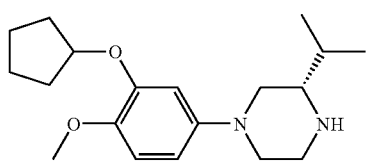

Prepared by the method outlined for Example 1 using 2(R)-N1 BOC-2-(isopropyl)-piperazine as piperazine component. Oils (54 and 71%). LC/MS 8.32 and 4.62 min, [M+1]$^+$ 419 and 319.

Example 23

Preparation of Compound 71, (S)-1-(3-Cyclopentyloxy-4-methoxy-phenyl)-3-isobutyl-piperazine

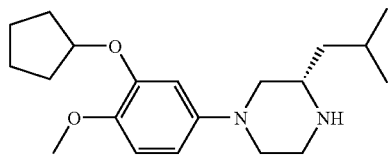

Prepared by the method outlined for Example 1 using 2(R)-N1 BOC-2-(isobutyl)-piperazine as piperazine component. Oils (63 and 94%). LC/MS 8.41 and 4.58 min, [M+1]$^+$ 433 and 333.

Example 24

Preparation of Compound 72, (S)-3-Cyclohexylmethyl-1-(3-cyclopentyloxy-4-methoxy-phenyl)-piperazine

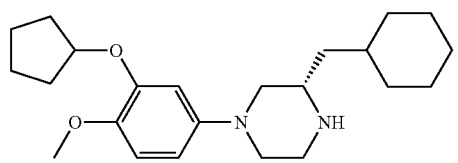

Prepared by the method outlined for Example 1 using 2(S)-N1 BOC-2-(cyclohexylmethyl)-piperazine as piperazine component. Oils (49 and 88%). LC/MS 9.36 and 5.30 min, [M+1]$^+$ 473 and 373.

Example 25

Preparation of Compound 73, 3-[(S)-4-(3-Cyclopentyloxy-4-methoxy-phenyl)-piperazin-2-ylmethyl]-1H-indole

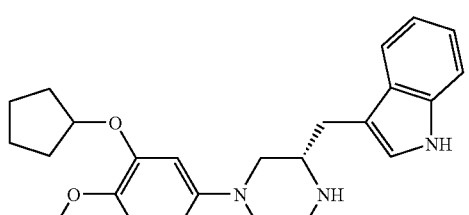

Prepared by the method outlined for Example 1 using 2(R)-N1 BOC-2-(3-indolylmethyl)-piperazine as piperazine component. The BOC protected intermediate was chromatographically purified with a 2.5% then 7.5% MeOH/CH$_2$Cl$_2$ solvent system. Oils (25 and 92%). LC/MS 5.72 and 455 min, [M+1]$^+$ 506 and 406.

Example 26

Preparation of Preparation of Compound 74, (S)-3-Benzyl-1-(3-cyclopentyloxy-4-methoxy-phenyl)-[1,4]diazepane

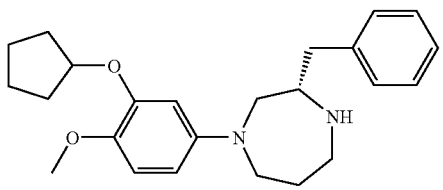

Prepared by the method outlined for Example 1 using (S)-2-Benzyl-[1,4]diazepane-1-carboxylic acid tert-butyl ester as piperazine component. Oils (42 and 92%). LC/MS 7.99 and 5.07 min, [M+1]$^+$ 481 and 381.

Example 27

Preparation of Compound 75, (R)-3-Benzyl-1-(3-cyclopentyloxy-4-methoxy-phenyl)-[1,4]diazepane

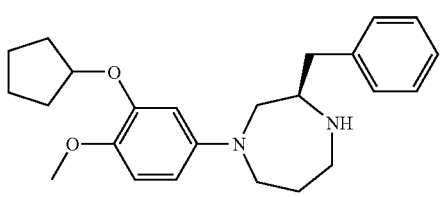

Prepared by the method outlined for Example 1 using (R)-2-Benzyl-[1,4]diazepane-1-carboxylic acid, tert-butyl ester as piperazine component. Oils (29 and 93%). LC/MS 7.96 and 5.03 min, [M+1]$^+$ 481 and 381.

Example 28

Preparation of Preparation of Compound 76, (S)-5-Benzyl-1-(3-cyclopentyloxy-4-methoxy-phenyl)-[1,4]diazepane

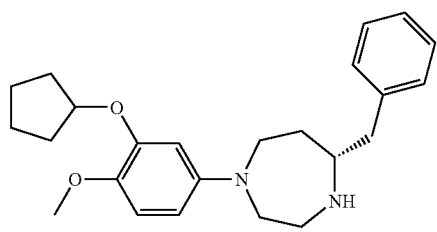

Prepared by the method outlined for Example 1 using (S)-7-Benzyl-[1,4]diazepane-1-carboxylic acid, tert-butyl ester as piperazine component. Oils (23 and 99%). LC/MS 7.42 and 4.91 min, [M+1]$^+$ 481 and 381.

Example 29

Preparation of Compound 77, (R)-5-Benzyl-1-(3-cyclopentyloxy-4-methoxy-phenyl)-[1,4]diazepane

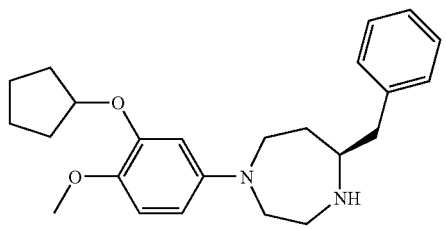

Prepared by the method outlined for Example 1 using (R)-7-Benzyl-[1,4]diazepane-1-carboxylic acid, tert-butyl ester as piperazine component. Oils (16 and 91%). LC/MS 7.43 and 4.89 min, [M+1]$^+$ 481 and 381.

Example 30

Preparation of Compound 78, 1-(3-Cyclopentyloxy-4-methoxy-phenyl)-piperazine

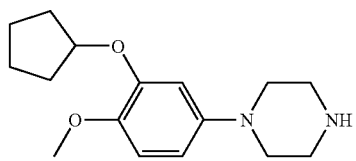

Prepared by the method outlined for Example 1 using N-BOC-piperazine as piperazine component. Oils (65% for two steps). LC/MS 4.11 min, [M+1]$^+$ 277.

Example 31

Preparation of Compound 79, (S)-2-Benzyl-4-(3-cyclopentyloxy-4-methoxy-phenyl)-morpholine

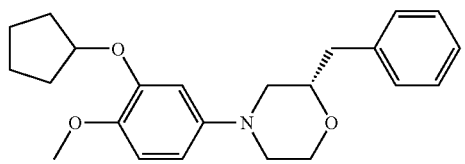

Prepared by the coupling method outlined for Example 1 using 2(S)-2-(benzyl)-morpholine as the amine component. Oil (29%). LC/MS 7.27 min, [M+1]$^+$ 368.

Example 32

Preparation of Compound 80, 4-[(S)-3-benzyl-1-piperzinyl]-7-methoxy-spiro[benzofuran-2(3H), 1'-cyclopentane]

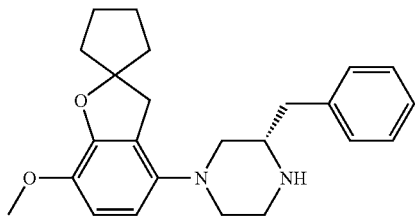

Prepared by the method outlined for Example 1 using 4-bromo-7-methoxy-spiro[benzofuran-2(3H), 1'-cyclopentane] (CAS [185244-55-7]) as the aryl halide and 2(S)-N1 BOC-2-(benzyl)-piperazine as the amine component. Oil (79% for two steps). LC/MS 5.02 min, [M+1]$^+$ 379.

Example 33

Preparation of Compound 81, 6-((S)-3-Benzyl-piperazin-1-yl)-1-cyclopentyl-3-methyl-1H-indazole

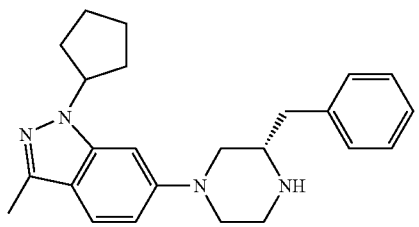

Prepared by the method outlined for Example 1 using 6-bromo-1-cyclopentyl-3-methyl-1H-indazole as the aryl halide and 2(S)-N1 BOC-2-(benzyl)-piperazine as the amine component. Oils (81 and 76%). LC/MS 5.13 min, [M+1]$^+$ 375.

Example 34

Preparation of Compound 82, 1-Cyclopentyl-3-ethyl-6-piperazin-1-yl-1H-indazole

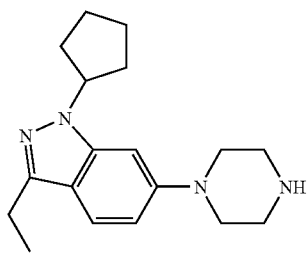

Prepared by the method outlined for Example 1 using 6-bromo-1-cyclopentyl-3-ethyl-1H-indazole (CAS [199172-02-6]) as the aryl halide and N BOC-piperazine as the amine component. Oil and gum (88% for two steps). LC/MS 4.56 min, [M+1]$^+$ 299.

Example 35

Preparation of Compound 83, 6-((S)-3-Benzyl-piperazin-1-yl)-1-cyclopentyl-3-ethyl-1H-indazole

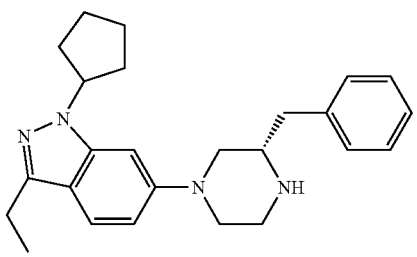

Prepared by the method outlined for Example 1 using 6-bromo-1-cyclopentyl-3-ethyl-1H-indazole (CAS [199172-02-6]) as the aryl halide and 2(S)-N1 BOC-2-(benzyl)-piperazine as the amine component. Oil (86 and 90%). LC/MS 5.28 min, [M+1]$^+$ 389.

Example 36

Preparation of Compound 84, (S)-2-Benzyl-4-(3-cyclopentyloxy-4-methoxy-phenyl)-1-methyl-piperazine

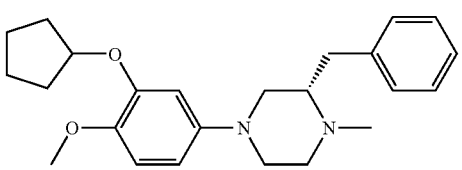

A solution of (S)-3-Benzyl-1-(3-cyclopentyloxy-4-methoxy-phenyl)-piperazine (Example 2) (73 mg, 0.2 mmol) in CH$_2$Cl$_2$ (5 mL) was treated with a 37% aqueous formaldehyde solution (16.4 uL, 0.22 mmol) and stirred for 5 min after which time solid sodium triacetoxyborohydride (64 mg, 0.3 mmol) was added. The suspension was then stirred for 3 hr then quenched with a saturated aqueous NaHCO$_3$ solution (2 mL). The organic component was separated, dried over MgSO$_4$, filtered, and evaporated to an oil which was purified by silica gel flash chromatography with 5% MeOH/CH$_2$Cl$_2$ as eluant to afford product as a burgundy oil (69 mg, 91%). $^1$H NMR (CDCl$_3$) 1.54-1.61 (m, 2H), 1.77-1.85 (m, 6H), 2.57 (s, 3H), 2.60-2.67 (m, 3H), 3.02-3.13 (m, 3H), 3.22-3.32 (m, 2H), 3.76 (s, 3H), 4.59-4.62 (m, 1H), 3.76 (s, 3 H), 4.59-4.62 (m, 1H), 6.30 (dd, J=8.6, 2.9, 1H), 6.35 (d, J=8.6, 1H), 7.20-7.33 (m, 5H). $^{13}$C NMR 24.2 (CH$_2$), 33.0 (CH$_2$), 36.3 (CH$_2$), 42.9(CH$_3$), 50.2 (CH$_2$), 55.0 (CH$_2$), 55.1 (CH$_2$), 56.8 (CH$_3$), 63.7 (CH), 80.4 (CH), 106.2 (CH), 107.8(CH), 113.2(CH), 126.4 (CH) 128.6, 129.5 (CH), 139.0 (CH), 144.5, 146.1, 148.4. LC/MS 5.10 min, [M+1]$^+$ 381.

Example 37

Preparation of Compound 85, (S)-2-Benzyl-4-(3-cyclopentyloxy-4-methoxy-phenyl)-1-ethyl-piperazine

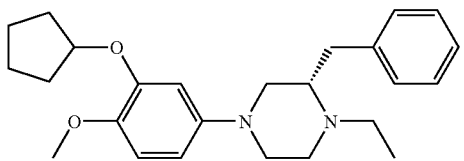

Prepared by the method outlined for Example 36 using acetaldehyde as the aldehyde component. Oil (84%). LC/MS 4.73 min, [M+1]$^+$ 395.

Example 38

Preparation of Compound 86, (S)-2-Benzyl-4-(3-cyclopentyloxy-4-methoxy-phenyl)-1-propyl-piperazine

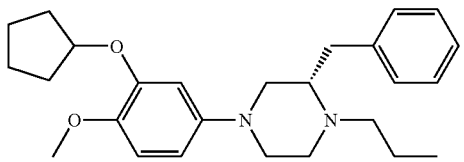

Prepared by the method outlined for Example 36 using propionaldehyde as the aldehyde component. Oil (95%). LC/MS 4.80 min, [M+1]$^+$ 409.

Example 39

Preparation of Compound 87, (S)-2-Benzyl-4-(3-cyclopentyloxy-4-methoxy-phenyl)-1-benzyl-piperazine

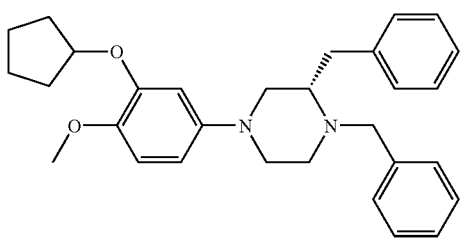

Prepared by the method outlined for Example 36 using benzaldehyde as the aldehyde component. Oil (50%). LC/MS 5.43 min, [M+1]$^+$ 457.

Example 40

Preparation of Compound 88, (S)-2-Benzyl-4-(3-cyclopentyloxy-4-methoxy-phenyl)-1-pyridin-2-ylmethyl-piperazine

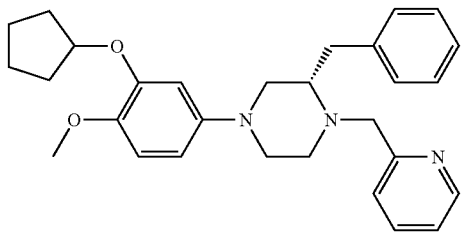

Prepared by the method outlined for Example 36 using 2-pyridinecarboxaldehyde as the aldehyde component. Oil (44%). LC/MS 5.38 min, [M+1]$^+$ 458.

Example 41

Preparation of Compound 89, (S)-2-Benzyl-4-(3-cyclopentyloxy-4-methoxy-phenyl)-1-pyridin-3-ylmethyl-piperazine

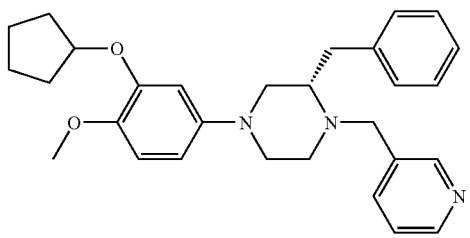

Prepared by the method outlined for Example 36 using 3-pyridinecarboxaldehyde as the aldehyde component. Oil (57%). LC/MS 5.07 min, [M+1]$^+$ 458.

Example 42

Preparation of Compound 90, (S)-2-Benzyl-4-(3-cyclopentyloxy-4-methoxy-phenyl)-1-pyridin-4-ylmethyl-piperazine

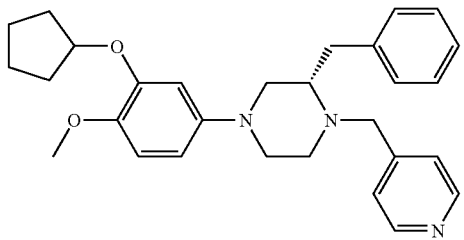

Prepared by the method outlined for Example 36 using 4-pyridinecarboxaldehyde as the aldehyde component. Oil (44%). LC/MS 5.21 min, [M+1]+ 458.

Example 43

Preparation of Compound 91, (S)-2-Benzyl-4-(3-cyclopentyloxy-4-methoxy-phenyl)-1-(3H-imidazol-4-ylmethyl)-piperazine

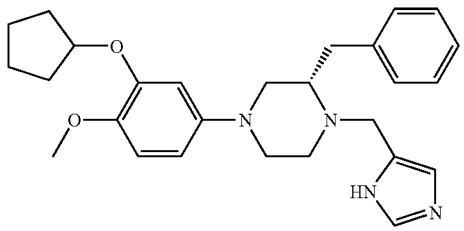

Prepared by the method outlined for Example 36 using 1-tritylimidazole-4-carboxaldehyde as the aldehyde component. Oil (69%) LC/MS 6.25 min, [M+1]+ 689. The trityl protected intermediate was deprotected by dissolving the intermediate (90 mg, 0.1345 mmol) in $CH_2Cl_2$ (0.5 mL) which was treated with triethylsilane (0.5 mL) followed by trifluoroacetic acid (1.0 mL). The reaction mixture was stirred for 2 h then evaporated to a residue which was triturated with a 10% EtOAc/hexane solution (4×1 mL). The residue was then partitioned between EtOAc (1 mL) and a saturated aqueous $K_2CO_3$ solution (0.5 mL). The organic component was separated, dried over $MgSO_4$, filtered, and evaporated to afford product as a foam (50 mg, 83%). LC/MS 4.50 min, [M+1]+ 447.

Example 44

Preparation of Compound 92, (S)-2-Benzyl-4-(3-cyclopentyloxy-4-methoxy-phenyl)-1-(1H-imidazol-2-ylmethyl)-piperazine

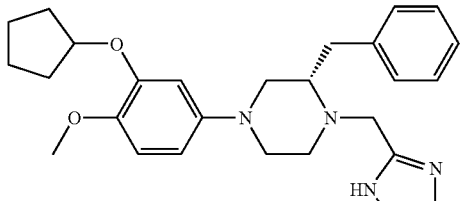

Prepared by the method outlined for Example 43 using 1-tritylimidazole-2-carboxaldehyde as the aldehyde component. Oil and foam (63 and 75%). LC/MS 6.20 and 4.77 min, [M+1]+ 689 and 447.

Example 45

Preparation of Compound 93, (S)-2-Benzyl-4-(3-cyclopentyloxy-4-methoxy-phenyl)-1-methanesulfonyl-piperazine

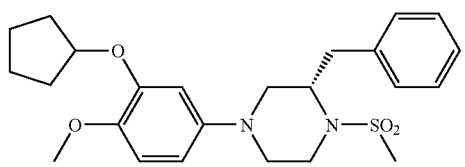

A solution of the bis-hydrochloride salt of (S)-3-Benzyl-1-(3-cyclopentyloxy-4-methoxy-phenyl)-piperazine (Example 2) (50 mg, 0.114 mmol) in pyridine (1 mL) was treated with methanesulfonyl chloride (26 µL, 0.341 mmol) and stirred at room temperature for 16 h. The reaction mixture was evaporated and partitioned between EtOAc (2 mL) and a saturated aqueous $NaHCO_3$ solution (2 mL). The organic component was separated, dried over $MgSO_4$, filtered, and evaporated to an oil which was purified by silica gel flash chromatography with 30% then 40% EtOAc/hexane as eluant to afford product as an oil (46 mg, 91%). $^1$H NMR ($CDCl_3$) 1.60-1.62 (M, 2H), 1.84-1.87 (m, 4H), 1.90-2.04 (m, 2H), 2.55 (s, 3H), 2.76-2.80 (m, 2H), 3.19-3.56 (m, 5H), 3.77 (m, 1H), 3.80 (s, 3H), 4.30 (br t, 1H), 4.71 (m, 1H), 6.42 (br d, J=8.1, 1H), 6.48 (br s, 1H), 6.78 (d, J=8.6, 1H), 7.23-7.36 (m, 5H). LC/MS 7.25 min, [M+1]+ 445.

Example 46

Preparation of Compound 94, (S)-2-Benzyl-4-(3-cyclopentyloxy-4-methoxy-phenyl)-1-ethanesulfonyl-piperazine

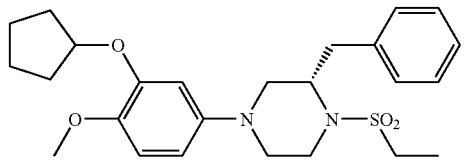

Prepared by the method outlined for Example 45 using ethanesulfonyl chloride as the sulfonyl chloride component. Oil (17%). LC/MS 7.41 min, [M+1]+ 459.

Example 47

Preparation of Compound 95, (S)-2-Benzyl-4-(3-cyclopentyloxy-4-methoxy-phenyl)-1-benzylsulfonyl-piperazine

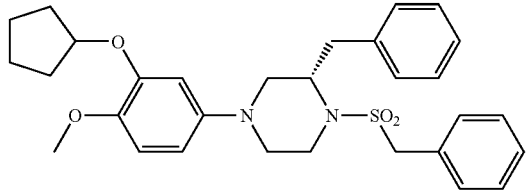

Prepared by the method outlined for Example 45 using benzylsulfonyl chloride as the sulfonyl chloride component. Oil (6%). LC/MS 7.82 min, [M+1]+ 521.

Example 48

Preparation of Compound 96, 1-[(S)-2-Benzyl-4-(3-cyclopentyloxy-4-methoxy-phenyl)-piperazin-1-yl]-ethanone

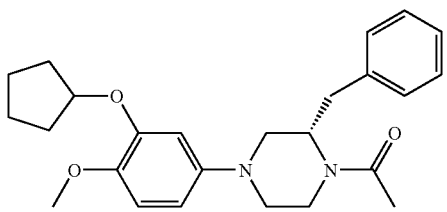

Prepared by the method outlined for Example 45 using acetic anhydride as reagent. Oil (97%). LC/MS 6.88 min, [M+1]+ 409.

Example 49

Preparation of Compound 97, (S)-2-Benzyl-4-(3-cyclopentyloxy-4-methoxy-phenyl)-piperazine-1-carboxylic acid ethylamide

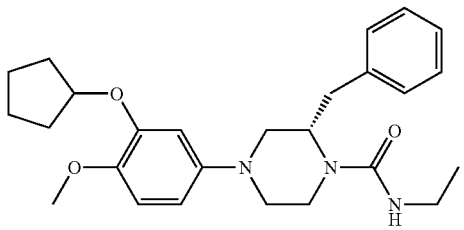

A solution of (S)-3-Benzyl-1-(3-cyclopentyloxy-4-methoxy-phenyl)-piperazine (Example 2) (73 mg, 0.2 mmol) in CH$_2$Cl$_2$ (0.5 mL) at 0° C. was treated with ethyl isocyanate (19 μL, 0.24 mmol) and stirred for 1 h, then evaporated and the residue purified by silica gel flash chromatography with 50% then 75% EtOAc/hexane as eluant to afford product as a foam (60 mg, 69%) $^1$H NMR (CDCl$_3$) 1.04 (t, J=7.2, 3H), 1.59-1.64 (m, 2H), 1.79-1.90 (m, 3H), 1.91-1.96 (m, 2H), 2.67-2.75 (m, 2H), 3.00-3.43 (m, 7H), 3.79 (s, 3H), 3.93 (br d, J=12.5, 1H), 4.13-4.27 (m, 2H), 4.70-4.73 (m, 1H), 6.40 (br d, J=7.5, 1H), 6.49 (br s, 1H), 6.78 (d, J=8.8, 1H), 7.22-7.35 (m, 5H). LC/MS 6.86 min, [M+1]+ 438.

Example 50

Preparation of Compound 98, (S)-2-Benzyl-4-(3-cyclopentyloxy-4-methoxy-phenyl)-piperazine-1-carboxylic acid ethyl ester

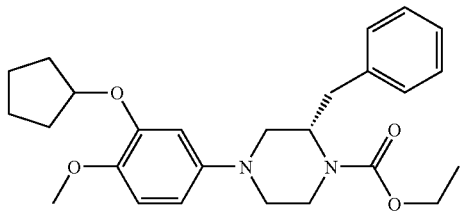

A solution of (S)-3-Benzyl-1-(3-cyclopentyloxy-4-methoxy-phenyl)-piperazine (Example 2) (73 mg, 0.2 mmol) in THF (0.5 mL) at room temperature was treated with triethylamine (28 μL, 0.2 mmol) followed by ethyl chloroformate (19 μL, 0.2 mmol). The reaction mixture was stirred for 2 h then diluted with EtOAc (2 mL) followed by a saturated aqueous NaHCO$_3$ solution (1 mL). The organic phase was isolated and further washed with an additional portion of a saturated aqueous NaHCO$_3$ solution (1 mL) followed by a brine solution (1 mL). The organic component was dried over MgSO$_4$, filtered, and evaporated to an oil which was purified by silica gel flash chromatography with 10% then 30% EtOAc/hexane as eluant to afford product as an oil (30 mg, 34%). $^1$H NMR (CDCl$_3$) 1.25 (t, J=7.2, 3H), 1.60-1.65 (m, 2H), 1.79-1.89 (m, 3H), 1.92-2.00 (m, 2H), 2.60-2.72 (m, 2H), 2.95 (dd, J=12.9, 4.8, 1H), 3.20-3.28 (m, 2H), 3.33-3.42 (m, 2H), 3.79 (s, 3H), 4.08-4.13 (m, 3H), 4.40 (br s, 1H), 4.69-4.72 (m, 1H), 6.39 (dd, J=8.6, 2.4, 1H), 6.47 (s, 1H), 6.77 (d, J=8.6, 1H), 7.22-7.34 (m, 5H). LC/MS 7.81 min, [M+1]+ 439.

Example 51

Preparation of Compound 99, 1-[(S)-2-Benzyl-4-(3-cyclopentyloxy-4-methoxy-phenyl)-piperazin-1-yl]-2-hydroxy-ethanone

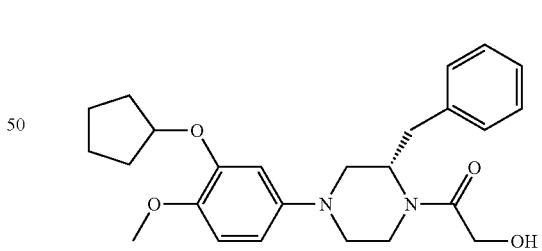

A solution of (S)-3-Benzyl-1-(3-cyclopentyloxy-4-methoxy-phenyl)-piperazine (Example 2) (73 mg, 0.2 mmol) in THF (1.5 mL) at room temperature was treated with triethylamine (42 μL, 0.3 mmol) followed by benzyloxyacetyl chloride (19 μL, 0.2 mmol). The reaction mixture was stirred for 2 h then diluted with EtOAc (2 mL) and water (2 mL). The organic phase was isolated and further washed with an additional portion of a water (2 mL) followed by a brine solution (2 mL). The organic component was dried over MgSO$_4$, filtered, and evaporated to an oil which was purified by silica gel flash chromatography with 20% then 40% EtOAc/hexane as eluant to afford coupled product as an oil (69 mg, 67%). LC/MS 7.64 min, [M+1]+ 515. The intermediate benzyloxy ether (60 mg, 0.117 mmol) was dissolved in MeOH (20 mL), purged with a stream of nitrogen, treated with 20% Pd/C (140 mg, 50% water content), and hydrogenated under 40 psi pressure of hydrogen for 4 h. The crude reaction mixture was then purged with nitrogen, filtered, evaporated, and purified by silica gel flash chromatography with 40% then 75% EtOAc/hexane as eluant to afford product as an oil (9 mg, 18%). LC/MS 6.55 min, [M+1]+ 425.

Example 52

Preparation of Compound 100, 2-Amino-1-[(S)-2-benzyl-4-(3-cyclopentyloxy-4-methoxy-phenyl)-piperazin-1-yl]-ethanone, hydrochloride salt

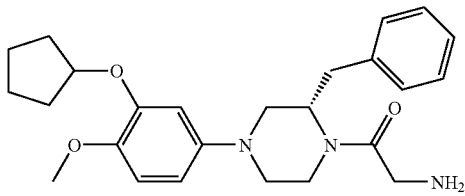

A solution of (S)-3-Benzyl-1-(3-cyclopentyloxy-4-methoxy-phenyl)-piperazine (Example 2) (73 mg, 0.2 mmol) and BOC-glycine (35 mg, 0.2 mmol) in DMF (1.0 mL) at room temperature was treated with diisopropylethylamine (35 µL, 0.2 mmol) followed by HATU (84 mg, 0.22 mmol). The reaction mixture was stirred for 2 h then partitioned between EtOAc (10 mL) and a saturated aqueous NaHCO$_3$ solution (10 mL). The organic component was isolated and further washed with brine (10 mL) then dried over MgSO$_4$, filtered, and evaporated to an oil which was purified by silica gel flash chromatography with 40% EtOAc/hexane as eluant to afford BOC-containing coupled product as a foam (85 mg, 81%). LC/MS 7.46 min, [M+1]+ 524. The BOC-protected intermediate was dissolved in a 4 N solution of hydrogen chloride in dioxane and stirred for 2 h then evaporated to a solid which was filtered and washed with diethyl ether to afford product as a colorless solid (42 mg, 49% based on trihydrochloride salt). LC/MS 4.66 min, [M+1]+ 424.

Example 53

Preparation of Compound 101, 1-[(S)-2-Benzyl-4-(3-cyclopentyloxy-4-methoxy-phenyl)-piperazin-1-yl]-2-methylamino-ethanone, hydrochloride salt

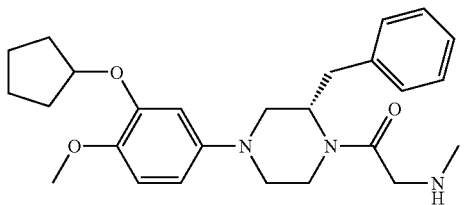

Prepared by the method outlined for Example 52 using BOC-sarcosine as the acid coupling component. Foam and solid (74 and 86%, based on trihydrochloride salt). LC/MS 7.46 and 4.72 min, [M+1]+ 539 and 438.

Example 54

Preparation of Compound 102, 4-[(1-((S)-3-benzyl-4-piperazin-1-yl)-2-hydroxy-ethanone)]-7-methoxy-spiro[benzofuran-2(3H), 1'-cyclopentane]

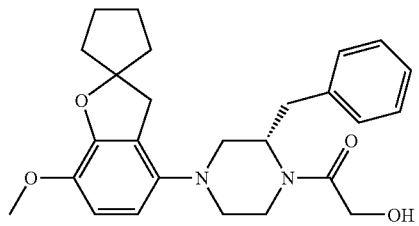

Prepared by the method outlined for Example 51 using compound 80 (Example 32) as the amine coupling component. Oils (67 and 37%). LC/MS 7.60 and 6.68 min, [M+1]+ 527 and 437.

Example 55

Preparation of Compound 103, 1-[(S)-2-Benzyl-4-(1-cyclopentyl-3-ethyl-1H-indazol-6-yl)-piperazin-1-yl]-2-hydroxy-ethanone

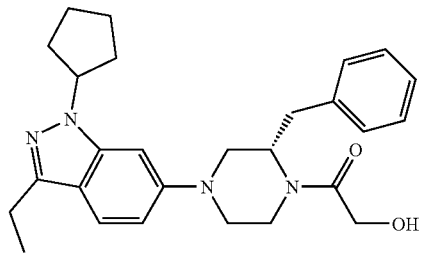

Prepared by the method outlined for Example 51 using 6-((S)-3-Benzyl-piperazin-1-yl)-1-cyclopentyl-3-ethyl-1H-indazole (Example 35) as the amine coupling component. Oils (73 and 49%). LC/MS 8.03 and 7.12 min, [M+1]+ 537 and 447.

Example 56

Preparation of Compound 104, 2-[(S)-2-Benzyl-4-(3-cyclopentyloxy-4-methoxy-phenyl)-piperazin-1-yl]-acetamide

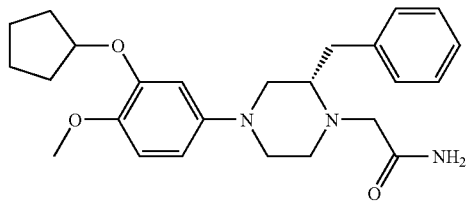

A solution of the bishydrochloride salt of (S)-3-Benzyl-1-(3-cyclopentyloxy-4-methoxy-phenyl)-piperazine (Example 2) (110 mg, 0.25 mmol) in THF (2 mL) at room temperature was treated with diisopropylethylamine (165 µL, 1.0 mmol) followed by 2-bromoacetamide (42 mg, 0.3 mmol). The reaction mixture was heated at 50° C. for 8 h and an additional amount of bromide (42 mg, 0.3 mmol) then added. The reaction mixture was then stirred for an additional 16 h at room temperature and evaporated. The crude reaction was then partitioned between EtOAc (3 mL) and a saturated aqueous NaHCO$_3$ solution (3 mL). The organic phase was isolated and further washed with an additional portion of a saturated aqueous NaHCO$_3$ solution (3 mL) and brine (2×3 mL).

The organic component was dried over MgSO$_4$, filtered, and evaporated to an oil which was purified by silica gel flash chromatography with 80% EtOAc/hexane then 5% MeOH/EtOAc as eluant to afford product as an oil (23 mg, 22%). LC/MS 5.09 min, [M+1]$^+$ 424.

Example 57

Preparation of Compound 105, [(S)-2-Benzyl-4-(3-cyclopentyloxy-4-methoxy-phenyl)-piperazin-1-yl]-acetic acid methyl ester

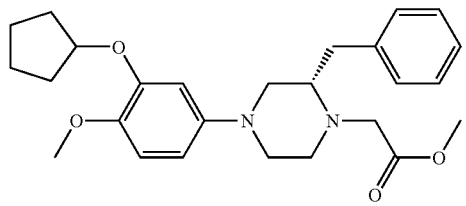

A solution of the bishydrochloride salt of (S)-3-Benzyl-1-(3-cyclopentyloxy-4-methoxy-phenyl)-piperazine (Example 2) (110 mg, 0.25 mmol) in THF (2 mL) at room temperature was treated with diisopropylethylamine (165 µL, 1.0 mmol) followed by 2-bromo methylacetate (95 µL, 1.0 mmol). The reaction mixture was stirred for 16 h at room temperature and evaporated. The crude reaction was then partitioned between EtOAc (3 mL) and a saturated aqueous NaHCO$_3$ solution (1 mL). The organic phase was isolated and further washed with an additional portion of a saturated aqueous NaHCO$_3$ solution (2×2 mL) and brine (2×2 mL). The organic component was dried over MgSO$_4$, filtered, and evaporated to an oil, which was purified by silica gel flash chromatography with 25% EtOAc/hexane as eluant to afford product as an oil (82 mg, 75%). $^1$H NMR (CDCl$_3$) 1.56-1.58 (m, 2H), 1.78-2.04 (m, 6H), 2.66-2.75 (m, 2H), 2.90-3.14 (m, 6H), 31.9-3.24 (m, 1H), 3.58 (s, 2H), 3.76 (s, 3H), 3.76 (s, 3H), 4.62 (m, 1H), 6.34 (dd, J=8.6, 2.6, 1H), 6.73 (d, J=8.8, 1H), 7.18-7.32 (m, 5H). $^{13}$C NMR 24.2 (CH$_2$), 33.0 (CH$_2$), 35.2 (CH$_2$), 50.2 (CH$_2$), 51.5 (CH$_3$), 51.9 (CH$_2$), 55.0 (CH$_2$), 55.5 (CH$_2$), 56.8 (CH$_3$), 60.5 (CH), 76.8 (CH), 106.4 (CH), 108.0 (CH), 113.3 (CH), 126.5 (CH) 128.7 (CH), 129.5 (CH), 139.0, 144.6, 146.2, 148.4, 171.2. LC/MS 5.74 min, [M+1]$^+$ 439.

Example 58

Preparation of Compound 106, 2-[(S)-2-Benzyl-4-(3-cyclopentyloxy-4-methoxy-phenyl)-piperazin-1-yl]-ethanol

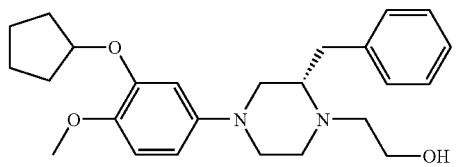

A solution of [(S)-2-Benzyl-4-(3-cyclopentyloxy-4-methoxy-phenyl)-piperazin-1-yl]-acetic acid methyl ester (Example 57) (110 mg, 0.25 mmol) in THF (2 mL) at room temperature was treated with a 1 N THF solution of lithium aluminum hydride (750 µL, 0.75 mmol) and allowed to stir for 12 h. The reaction mixture was quenched with an aqueous 15% NaOH solution (250 µL) followed by water (250 µL) and THF (2 mL). the reaction mixture was then treated with MgSO$_4$, filtered, and evaporated. The residue was then dissolved in EtOAc (3 mL), retreated with MgSO$_4$, filtered, and evaporated to afford product as an oil (75 mg, 73%). $^1$H NMR (CDCl$_3$) 1.58-1.62 (m, 2H), 1.67-1.88 (m, 6H), 2.74-3.22 (m, 12H), 3.65-3.76 (m, 2H), 3.78 (s, 3H), 4.64-4.67 (m, 1H), 6.34 (dd, J=8.6, 2.9, 1H), 6.40 (d, J=2.6, 1H), 6.75 (d, J=8.6, 1H), 7.20-7.33 (m, 5H). $^{13}$C NMR 24.2 (CH$_2$), 33.0 (CH$_2$), 33.0 (CH$_2$), 48.4 (CH$_2$), 49.7 (CH$_2$), 53.9 (CH$_2$), 55.5 (CH$_2$), 56.9 (CH$_3$), 58.1 (CH$_2$), 61.6 (CH), 80.5 (CH), 106.5 (CH), 108.1 (CH), 113.4 (CH), 126.5 (CH) 128.8 (CH), 129.5 (CH), 139.6, 144.7, 146.5, 148.5. LC/MS 4.81 min, [M+1]$^+$ 411.

Example 59

Preparation of Compound 107, [(S)-2-Benzyl-4-(3-cyclopentyloxy-4-methoxy-phenyl)-piperazin-1-yl]-acetic acid

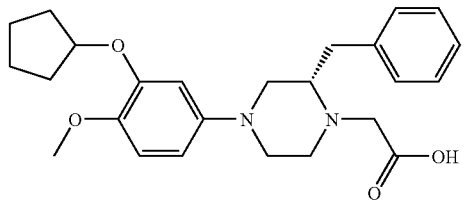

A solution of [(S)-2-Benzyl-4-(3-cyclopentyloxy-4-methoxy-phenyl)-piperazin-1-yl]-acetic acid methyl ester (Example 57) (342 mg, 0.78 mmol) in THF (5 mL) at room temperature was treated with an aqueous solution (1 mL) containing lithium hydroxide monohydrate (36 mg, 0.858 mmol). The reaction mixture was allowed to stir for 2 h and then evaporated to a small volume. The reaction mixture was then dissolved in water (5 mL) and the pH adjusted to ~7 with 1 N HCl to precipitate product. The precipitate was then triturated with water (2×5 mL) and dried under a stream of nitrogen to afford product as a colorless solid (318 mg, 96%). $^1$H NMR (CDCl$_3$) 1.43-1.57 (m, 2H), 1.77-1.79 (m, 6H), 3.02-3.15 (m, 2H), 3.27 (br s, 2H), 3.51 (br s, 1H), 3.74 (s, 3H), 3.77-3.89 (m, 2H), 4.57-4.59 (m, 1H), 6.24-6.31 (m, 2H), 6.55 (br s, OH), 6.67 (d, J=8.6, 1H) 7.18-7.27 (m, 5H). LC/MS 5.34 min, [M+1]+ 425.

Example 60

Preparation of Compound 108, 4-[(1-((S)-3-benzyl-4-piperazin-1-yl)-acetic acid)]-7-methoxy-spiro[benzofuran-2(3H),1'-cyclopentane]

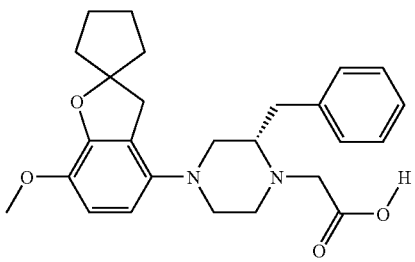

Prepared by the methods outlined for Examples 57/59 using compound 80 (Example 32) as the amine coupling component. Oil and tan solid (65 and 98%). LC/MS 5.65 and 5.29 min, [M+1]+ 452 and 437.

Example 61

Preparation of Compound 109, [(S)-2-Benzyl-4-(1-cyclopentyl-3-ethyl-1H-indazol-6-yl)-piperazin-1-yl]-acetic acid

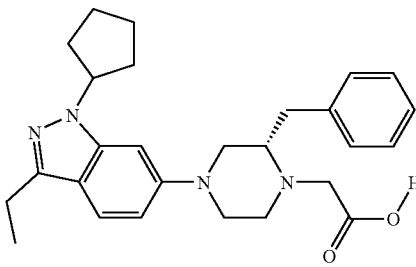

Prepared by the methods outlined for Examples 57/59 using 6-((S)-3-Benzyl-piperazin-1-yl)-1-cyclopentyl-3-ethyl-1H-indazole (Example 35) as the amine coupling component. Oil and tan solid (77 and 94%). LC/MS 6.37 and 5.65 min, [M+1]+ 462 and 447.

Example 62

Preparation of Compound 110, 2-[(S)-2-Benzyl-4-(3-cyclopentyloxy-4-methoxy-phenyl)-piperazin-1-yl]-N-methyl-acetamide

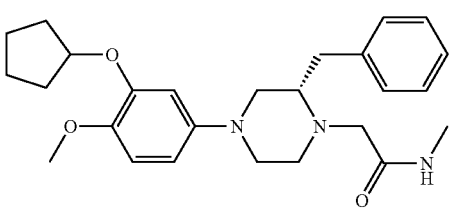

A solution of [(S)-2-Benzyl-4-(3-cyclopentyloxy-4-methoxy-phenyl)-piperazin-1-yl]-acetic acid (Example 59) (21.2 mg, 0.05 mmol) in CH$_2$Cl$_2$ (0.5 mL) at 0° C. was treated with DMAP (~1 mg) and DCC (11.3 mg, 0.055 mmol) followed 5 min later by a 2 M THF solution of methylamine (30 µL, 0.06 mmol). The reaction mixture was stirred for 16 h, evaporated, and purified by silica gel flash chromatography with 50% EtOAc/hexane, then 100% EtOAc, then 5% MeOH/EtOAc as eluant to afford product as an oil (6.4 mg, 29%). LC/MS 5.09 min, [M+1]+ 438.

Example 63

Preparation of Compound 111, [(S)-2-Benzyl-4-(3-cyclopentyloxy-4-methoxy-phenyl)-piperazin-1-yl]-acetic acid hydrazide

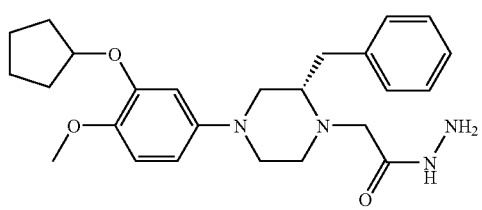

Prepared by the method outlined for Example 62 using hydrazine hydrate as the amine component. Oil (51%). LC/MS 4.84 min, [M+1]+ 439.

Example 64

Preparation of Compound 112, [(S)-2-Benzyl-4-(3-cyclopentyloxy-4-methoxy-phenyl)-piperazin-1-yl]-acetic acid N'-methyl-hydrazide

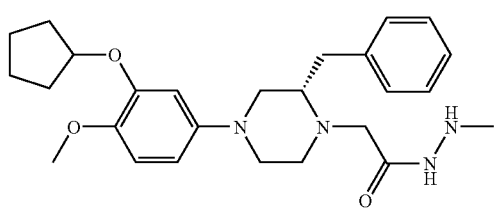

Prepared by the method outlined for Example 62 using methylhydrazine as the amine component. Oil (73%). LC/MS 4.90 min, [M+1]+ 453.

Example 65

Preparation of Compound 113, [(S)-2-Benzyl-4-(3-cyclopentyloxy-4-methoxy-phenyl)-piperazin-1-yl]-acetic acid N',N'-dimethyl-hydrazide

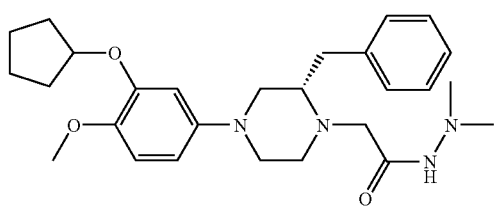

Prepared by the method outlined for Example 62 using unsym-dimethylhydrazine as the amine component. Oil (54%). LC/MS 5.04 min, [M+1]+ 467.

Example 66

Preparation of Compound 114, 2-[(S)-2-Benzyl-4-(3-cyclopentyloxy-4-methoxy-phenyl)-piperazin-1-yl]-N-methoxy-acetamide

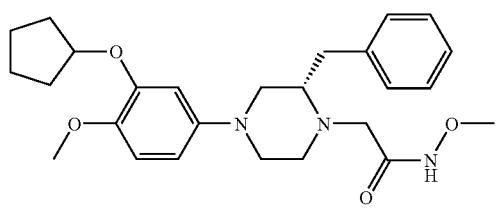

Prepared by the method outlined for Example 62 using O-methylhydroxylamine hydrochloride (with 1 equivalent of triethylamine to neutralize hydrochloride salt) as the amine component. Oil (57%). LC/MS 5.28 min, [M+1]+ 454.

Example 67

Preparation of Compound 115, 2-[(S)-2-Benzyl-4-(3-cyclopentyloxy-4-methoxy-phenyl)-piperazin-1-yl]-N-ethoxy-acetamide

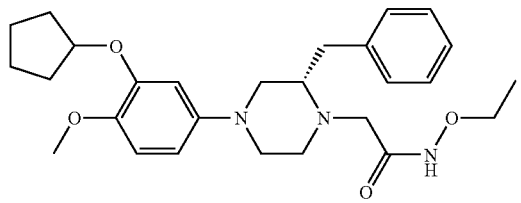

Prepared by the method outlined for Example 62 using O-ethylhydroxylamine hydrochloride (with 1 equivalent of triethylamine to neutralize hydrochloride salt) as the amine component. Oil (72%). LC/MS 5.30 min, [M+1]+ 468.

Example 68

Preparation of Compound 116, 2-[(S)-2-Benzyl-4-(3-cyclopentyloxy-4-methoxy-phenyl)-piperazin-1-yl]-N-isobutoxy-acetamide

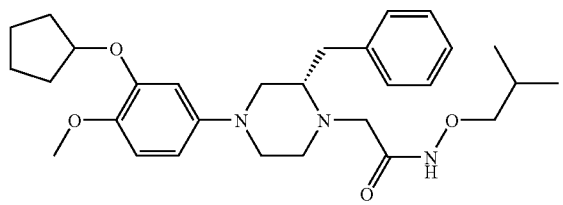

Prepared by the method outlined for Example 62 using O-isobutylhydroxylamine hydrochloride (with 1 equivalent of triethylamine to neutralize hydrochloride salt) as the amine component. Oil (67%). LC/MS 5.78 min, [M+1]+ 496.

Example 69

Preparation of Compound 117, 2-[(S)-2-Benzyl-4-(3-cyclopentyloxy-4-methoxy-phenyl)-piperazin-1-yl]-N-phenoxy-acetamide

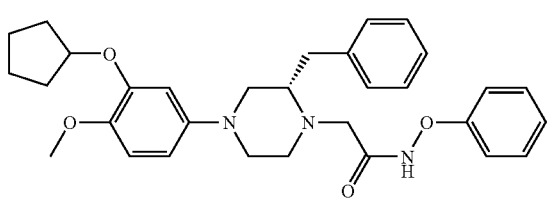

Prepared by the method outlined for Example 62 using O-phenylhydroxylamine hydrochloride (with 1 equivalent of triethylamine to neutralize hydrochloride salt) as the amine component. Oil (66%). LC/MS 6.13 min, [M+1]+ 516.

Example 70

Preparation of Compound 118, N-Allyloxy-2-[(S)-2-benzyl-4-(3-cyclopentyloxy-4-methoxy-phenyl)-piperazin-1-yl]-acetamide

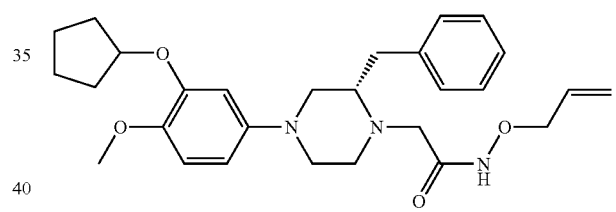

Prepared by the method outlined for Example 62 using O-allylhydroxylamine hydrochloride (with 1 equivalent of triethylamine to neutralize hydrochloride salt) as the amine component. Oil (71%). LC/MS 5.46 min, [M+1]+ 480.

Example 71

Preparation of Compound 119, 2-[(S)-2-Benzyl-4-(3-cyclopentyloxy-4-methoxy-phenyl)-piperazin-1-yl]-N-benzyloxy-acetamide

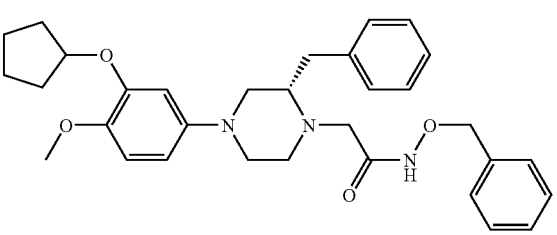

Prepared by the method outlined for Example 62 using O-benzylhydroxylamine hydrochloride (with 1 equivalent of triethylamine to neutralize hydrochloride salt) as the amine component. Oil (72%). LC/MS 5.90 min, [M+1]$^+$ 530.

Example 72

Preparation of Compound 120, 2-[(S)-2-Benzyl-4-(3-cyclopentyloxy-4-methoxy-phenyl)-piperazin-1-yl]-N-hydroxy-acetamide

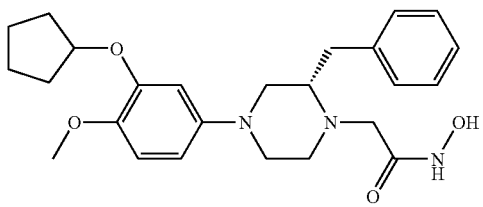

A solution of 2-[(S)-2-Benzyl-4-(3-cyclopentyloxy-4-methoxy-phenyl)-piperazin-1-yl]-N-benzyloxy-acetamide (Example 71) (30 mg, 0.0566 mmol) was dissolved in MeOH (10 mL), purged with a stream of nitrogen, treated with 20% Pd/C (100 mg, 50% water content), and hydrogenated under 40 psi pressure of hydrogen for 4 h. The crude reaction mixture was then purged with nitrogen, filtered, and evaporated. The crude product was then dissolved in chloroform (5 mL) and filtered through a nylon syringe filter to remove residual Pd/C. The organic solution was evaporated to afford product as a colorless foam (14 mg, 56%). LC/MS 5.03 min, [M+1]$^+$ 440.

Example 73

The following illustrate representative pharmaceutical dosage forms, containing a compound of formula I ('Compound X'), for therapeutic or prophylacetic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

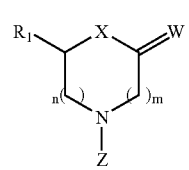

wherein:

$R_1$ is H, $(C_1\text{-}C_6)$alkyl, aryl, aryl$(C_1\text{-}C_6)$alkyl, indolyl;

n is 1;

m is 1;

W is O or two hydrogens;

X is N—Y—$R_4$;

Y is a direct bond or $CH_2$;

$R_4$ is H, $(C_1\text{-}C_6)$alkyl, $(C_1\text{-}C_6)$alkoxy, $(C_1\text{-}C_6)$alkanoyl, hydroxy, $(C_1\text{-}C_6)$alkoxycarbonyl, carboxy, aryl, or aryl$(C_1\text{-}C_6)$alkyl;

Z has the following formula:

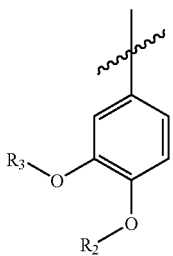

wherein $R_2$ is methyl and $R_3$ is cyclopropyl or cyclopentyl;

wherein the ring containing X is optionally substituted on carbon with one or more halo, $(C_1\text{-}C_6)$alkyl, or $(C_1\text{-}C_6)$alkoxy;

or a pharmaceutically acceptable salt thereof; and wherein if $R_1$ is H, $R_4$ cannot be aryl$(C_1\text{-}C_6)$alkyl.

2. A compound selected from the group consisting of:

(S)-3-Benzyl-1-(3-cyclopentyloxy-4-methoxy-phenyl)-piperazine;

(2S,5S)-5-Benzyl-1-(3-cyclopentyloxy-4-methoxy-phenyl)-2-methyl-piperazine;

(2R,5S)-5-Benzyl-1-(3-cyclopentyloxy-4-methoxy-phenyl)-2-methyl-piperazine;

(R)-6-Benzyl-4-(3-cyclopentyloxy-4-methoxy-phenyl)-piperazin-2-one;

(S)-6-Benzyl-4-(3-cyclopentyloxy-4-methoxy-phenyl)-piperazin-2-one;

(R)-3-Benzyl-1-(3-cyclopentyloxy-4-methoxy-phenyl)-piperazine;

(S)-1-(3-Cyclopentyloxy-4-methoxy-phenyl)-3-phenethyl-piperazine;

(R)-1-(3-Cyclopentyloxy-4-methoxy-phenyl)-3-phenethyl-piperazine;

(S)-1-(3-Cyclopentyloxy-4-methoxy-phenyl)-3-(3-phenyl-propyl)-piperazine;

(S)-1-(3-Cyclopentyloxy-4-methoxy-phenyl)-3-naphthalen-1-ylmethyl-piperazine;

(S)-1-(3-Cyclopentyloxy-4-methoxy-phenyl)-3-naphthalen-2-ylmethyl-piperazine;

(R)-1-(3-Cyclopentyloxy-4-methoxy-phenyl)-3-phenyl-piperazine;

(S)-1-(3-Cyclopentyloxy-4-methoxy-phenyl)-3-isopropyl-piperazine;

(S)-1-(3-Cyclopentyloxy-4-methoxy-phenyl)-3-isobutyl-piperazine;

1-(3-Cyclopentyloxy-4-methoxy-phenyl)-piperazine;

(S)-2-Benzyl-4-(3-cyclopentyloxy-4-methoxy-phenyl)-1-methyl-piperazine;

(S)-2-Benzyl-4-(3-cyclopentyloxy-4-methoxy-phenyl)-1-ethyl-piperazine;

(S)-2-Benzyl-4-(3-cyclopentyloxy-4-methoxy-phenyl)-1-benzyl-piperazine;

1-[(S)-2-Benzyl-4-(3-cyclopentyloxy-4-methoxy-phenyl)-piperazin-1-yl]-ethanone;

(S)-2-Benzyl-4-(3-cyclopentyloxy-4-methoxy-phenyl)-piperazine-1-carboxylic acid ethyl ester;

[(S)-2-Benzyl-4-(3-cyclopentyloxy-4-methoxy-phenyl)-piperazin-1-yl]-acetic acid methyl ester; and

[(S)-2-Benzyl-4-(3-cyclopentyloxy-4-methoxy-phenyl)-piperazin-1-yl]-acetic acid.

3. A compound selected from the group consisting of:

(S)-3-Benzyl-1-(3-cyclopentyloxy-4-methoxy-phenyl)-piperazine; and

[(S)-2-Benzyl-4-(3-cyclopentyloxy-4-methoxy-phenyl)-piperazin-1-yl]-acetic acid;

or a pharmaceutically acceptable salt thereof.

* * * * *